US010517871B2

(12) United States Patent
Zhang et al.

(10) Patent No.: US 10,517,871 B2
(45) Date of Patent: Dec. 31, 2019

(54) SURVIVIN-TARGETING ANTI-TUMOR AGENTS AND USES THEREOF

(71) Applicant: Indiana University Research and Technology Corporation, Indianapolis, IN (US)

(72) Inventors: Jian-Ting Zhang, Carmel, IN (US); Jing-Yuan Liu, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/573,867

(22) PCT Filed: May 13, 2016

(86) PCT No.: PCT/US2016/032473
§ 371 (c)(1),
(2) Date: Nov. 14, 2017

(87) PCT Pub. No.: WO2016/187046
PCT Pub. Date: Nov. 24, 2016

(65) Prior Publication Data
US 2018/0296557 A1 Oct. 18, 2018

Related U.S. Application Data

(60) Provisional application No. 62/162,291, filed on May 15, 2015.

(51) Int. Cl.
*A61K 31/4985* (2006.01)
*A61P 35/02* (2006.01)
*G01N 33/50* (2006.01)

(52) U.S. Cl.
CPC .......... *A61K 31/4985* (2013.01); *A61P 35/02* (2018.01); *G01N 33/5011* (2013.01)

(58) Field of Classification Search
CPC .................................................. A61K 31/4985
See application file for complete search history.

(56) References Cited

U.S. PATENT DOCUMENTS

| 7,196,083 | B2 | 3/2007 | Zhang et al. |
| 8,344,144 | B2 | 1/2013 | Machacek et al. |
| 2005/0143382 | A1 | 6/2005 | Aulinger-Fuchs et al. |

FOREIGN PATENT DOCUMENTS

| WO | WO2005/044270 | * | 5/2005 |
| WO | WO 2008106594 A2 | | 9/2008 |
| WO | WO 2013188848 A2 | | 12/2013 |

OTHER PUBLICATIONS

International Search Report and Written Opinion for International Application No. PCT/US16/32473 dated Aug. 8, 2016, 19 pages.

(Continued)

*Primary Examiner* — San Ming R Hui
(74) *Attorney, Agent, or Firm* — Faegre Baker Daniels LLP

(57) ABSTRACT

Methods for treating various cancers by administering one or more compounds that target the dimeric protein survivin are disclosed. Pharmaceutical compositions containing such compounds are also disclosed, along with general methods of identifying anti-cancer compounds that target oncogenic dimeric proteins. Exemplary compounds that can be used in the disclosed methods of treatment and pharmaceutical compositions have the chemical structure.

(Continued)

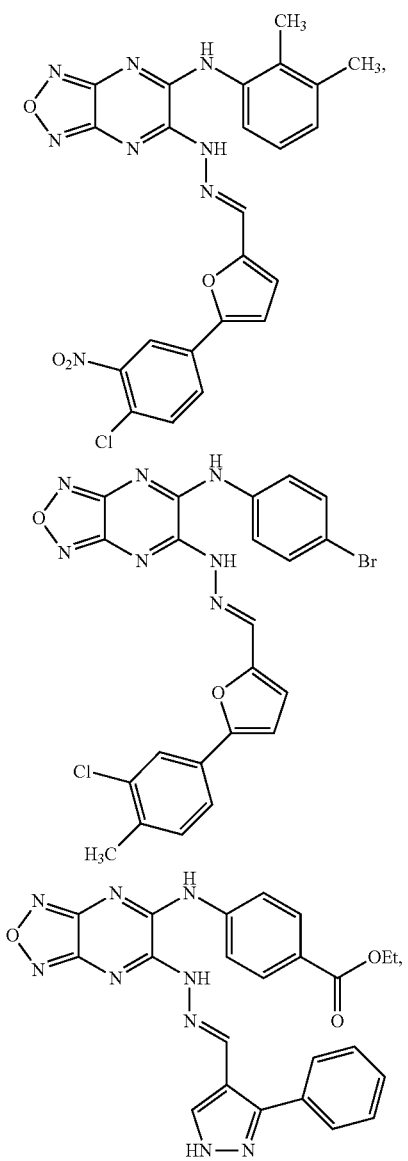
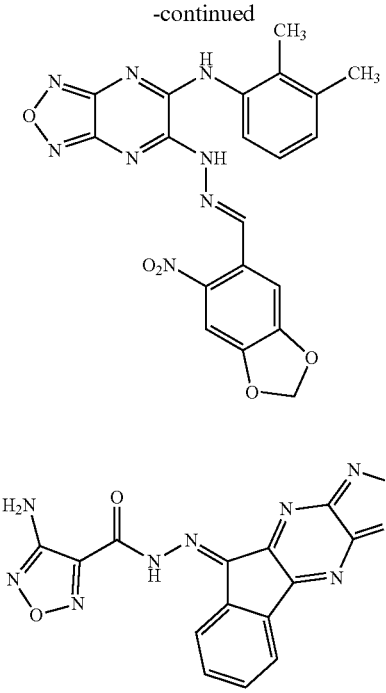

17 Claims, 17 Drawing Sheets

(56) References Cited

OTHER PUBLICATIONS

Asanuma et al., "Survivin Expression Is Regulated by Coexpression of Human Epidermal Growth Factor Receptor 2 and Epidermal Growth Factor Receptor via Phosphatidylinositol 3-Kinase/AKT Signaling Pathway in Breast Cancer Cells", Cancer Res 1005: 65: (23), p. 11018-11025, Dec. 1, 2015.

* cited by examiner

SURVIVIN-TARGETING ANTI-TUMOR AGENTS AND USES THEREOF

CROSS REFERENCE TO RELATED APPLICATIONS

This application represents the U.S. National Stage of International Application No. PCT/US2016/032473, filed May 13, 2016, which claims the benefit of U.S. Provisional Patent Application No. 62/162,291, filed May 15, 2015, which is incorporated herein by reference as if set forth in its entirety.

STATEMENT REGARDING FEDERALLY SPONSORED RESEARCH OR DEVELOPMENT

Not applicable.

FIELD

This disclosure relates to the use of compounds that target the dimeric protein survivin for treating cancer, and to the methods used to identify such compounds.

BACKGROUND

Survivin is a member of the Inhibitor of apoptosis (IAP) gene family containing a single Baculovirus IAP Repeat (BIR) domain, a zinc-finger fold, and an extended C-terminal helical coiled coil[1]. It is a homo-dimer of 16.5-kDa protein[2,3]. Ectopic survivin over-expression causes inhibition of cell death induced by intrinsic and extrinsic stimuli in cell lines[4-9] and in animals[10]. Survivin is over-expressed essentially in all cancers, but not expressed in most adult normal tissues[1,11]. Survivin has also been shown to contribute to radiotherapy and chemotherapy resistance, and inhibition of survivin sensitizes cancer cells to these treatments[12-14]. Treatments with molecular probes such as antisense oligonucleotide, ribozyme, siRNA, and dominant negative mutant all resulted in caspase-dependent cell death and increased apoptosis induced by radiation and anticancer drugs[14-19]. These findings have established survivin as an ideal target for discovery of anticancer therapeutics.

Unfortunately, survivin belongs to a group of proteins that are considered "undruggable" due to lack of enzymatic activities. Although small molecule inhibitors have been identified that would interfere with the function of this type of proteins by blocking their interaction with other essential proteins, these approaches have generally not led to promising drug candidates.

In the case of survivin, targeting its expression has been attempted as an alternative to targeting survivin protein directly. For example, YM155, a small molecule compound, has been identified to inhibit survivin expression by targeting its transcription[20]. However, several phase II trials of YM155 showed only limited or modest at best efficacy on human cancers[21]. An antisense oligonucleotide, LY2181308, that inhibits survivin expression has also been tested as a single agent in phase I trial for solid tumors[22] and in combination with docetaxel in phase II trial for castration-resistant prostate cancers[23]. Unfortunately, neither of these two trials showed any benefit of using LY2181308.

Thus, new inhibitors of survivin are clearly needed, perhaps based on a computational strategy to directly target the dimerization interface of survivin protein itself, a strategy that has not been attempted previously because survivin protein itself is considered "undruggable".

BRIEF SUMMARY

The inventor has determined that several survivin-targeting compounds inhibit cell survival at low concentration in two different human prostate cancer cell lines. Furthermore, one of these compounds was shown to inhibit cell survival at low concentration in 13 different human cancer cell lines broadly encompassing seven different classes of cancer, and was shown to be effective in suppressing xenograft tumor growth in an in vivo model.

Accordingly, in a first aspect, this disclosure encompasses a method of treating cancer by administering to a subject in need thereof a therapeutically effective amount of a composition comprising a survivin-targeting compound or a pharmaceutically acceptable salt thereof. Exemplary survivin-targeting compounds that could be used in the method include:

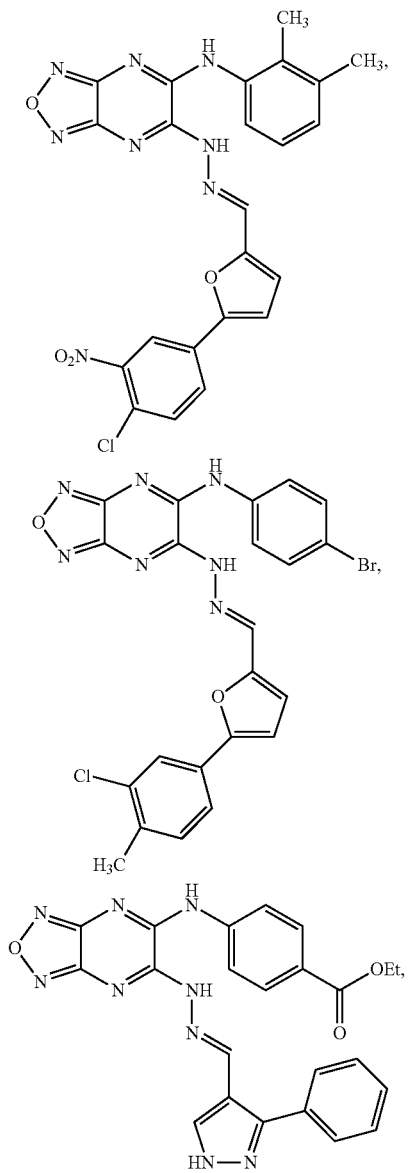

-continued

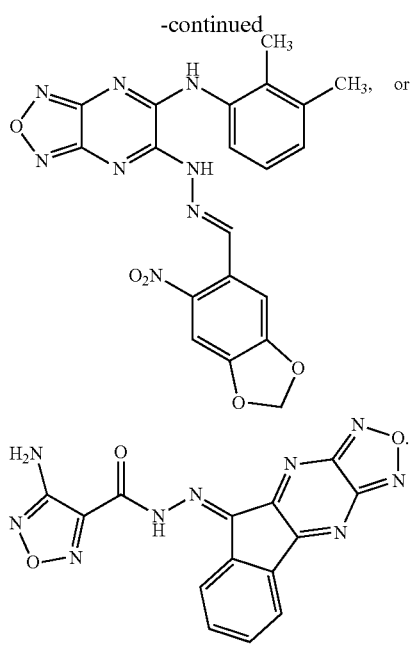

In some embodiments, the survivin-targeting compound is:

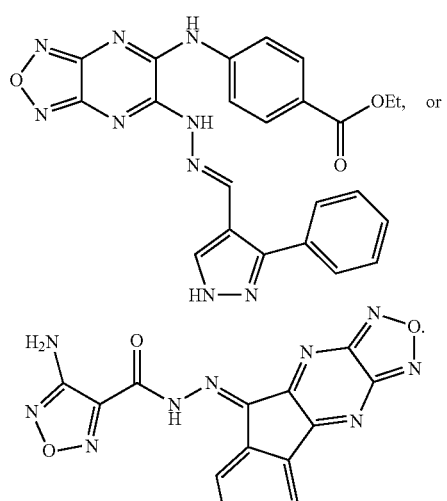

In some such embodiments, the survivin-targeting compound is:

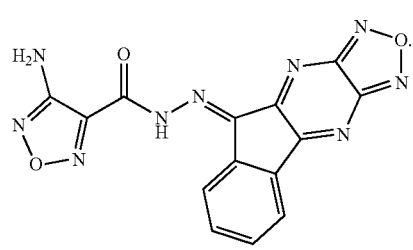 [SMILES: Nc1nonc1C(=O)N/N=C1\c2ccccc2-c2nc3nonc3nc21]

In some embodiments, the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

In some embodiments, the cancer that is treated is breast cancer, colon cancer, lung cancer, pancreatic cancer, prostate cancer, ovarian cancer, or leukemia. In some such embodiments, the cancer that is treated is prostate cancer.

In a second aspect, this disclosure encompasses a pharmaceutical composition that includes (a) one of the following survivin-targeting compounds or a pharmaceutically acceptable salt thereof:

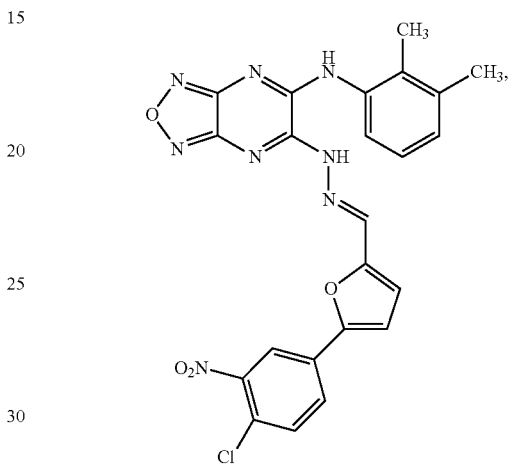

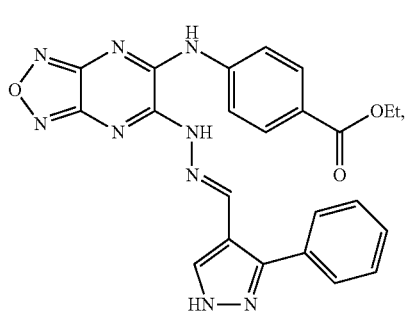

-continued

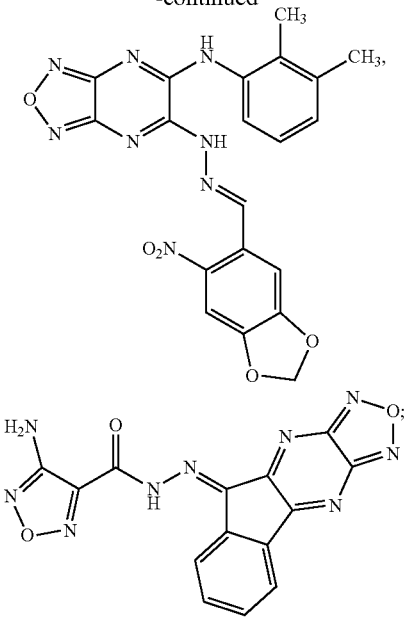

and (b) a pharmaceutically acceptable carrier.

In some embodiments, the survivin-targeting compound is:

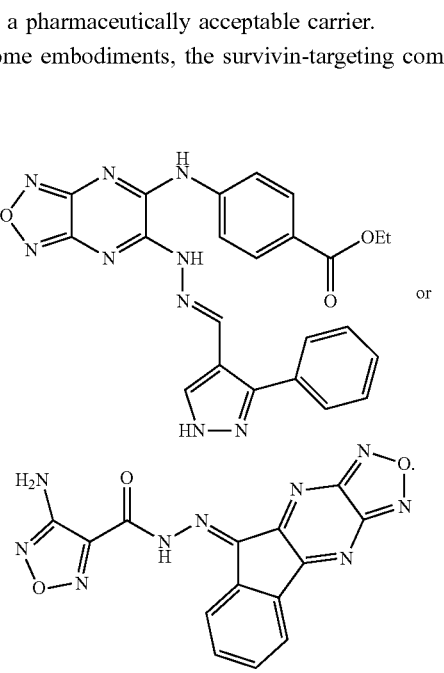

In some such embodiments, the survivin-targeting compound is:

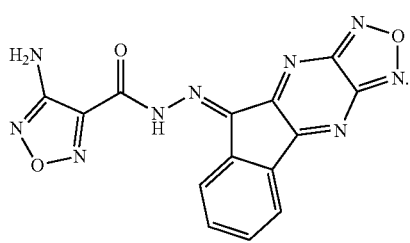 [SMILES: Nc1nonc1C(=O)N/N=C1\c2ccccc2-c2nc3nonc3nc21]

In a third aspect, this disclosure encompasses a survivin-targeting compound or a pharmaceutically acceptable salt thereof for use in treating cancer in a subject. Exemplary survivin-targeting compound that could be used include:

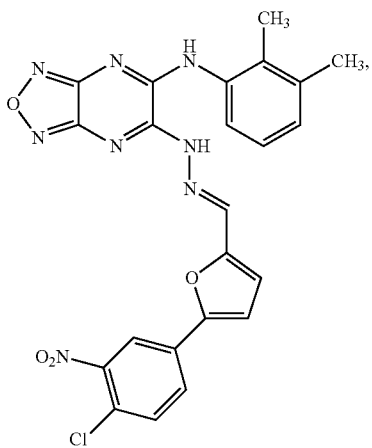

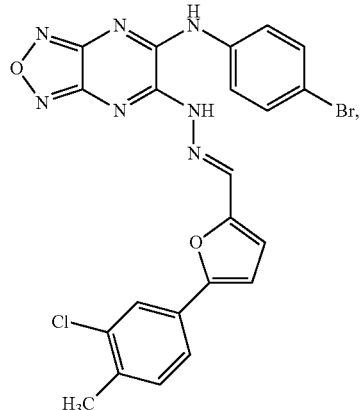

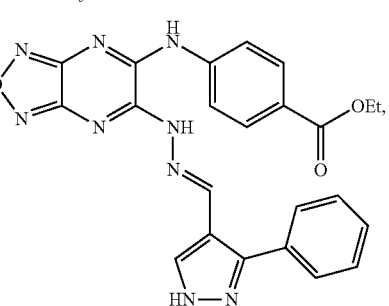

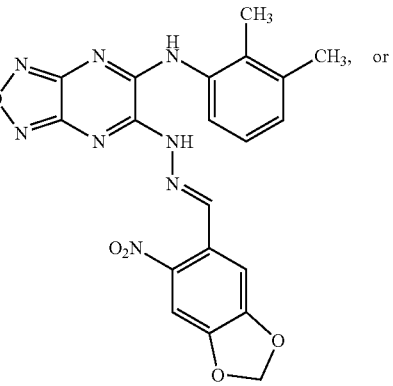

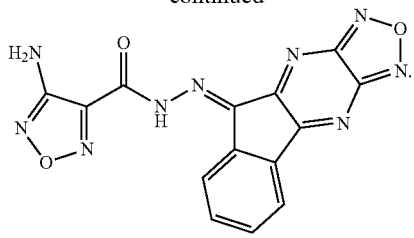

In some embodiments, the survivin-targeting compound is:

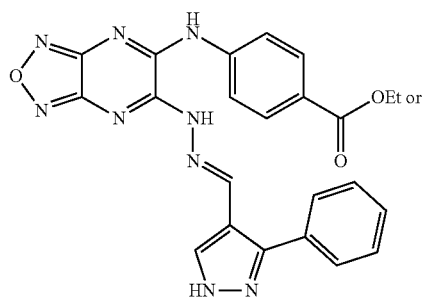

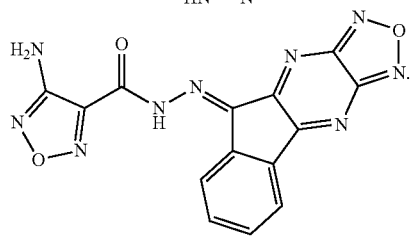

In some such embodiments, the survivin-targeting compound is:

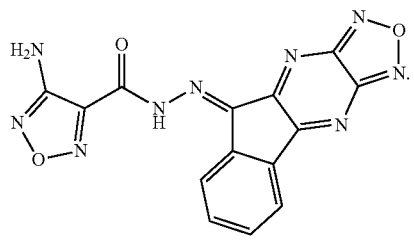 [SMILES: Nc1nonc1C(=O)N/N=C1\c2ccccc2-c2nc3nonc3nc21]

In some embodiments, the compound is for treating breast cancer, colon cancer, lung cancer, pancreatic cancer, prostate cancer, ovarian cancer, or leukemia. In some such embodiments, the compound is for use in treating prostate cancer.

In some embodiments, the compound is to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

In a fourth aspect, this disclosure encompasses a survivin-targeting compound or pharmaceutically acceptable salt thereof for use in manufacturing a medicament for treating cancer in a subject. Exemplary survivin-targeting compounds include:

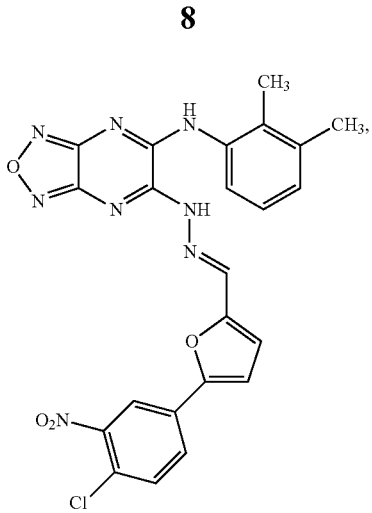

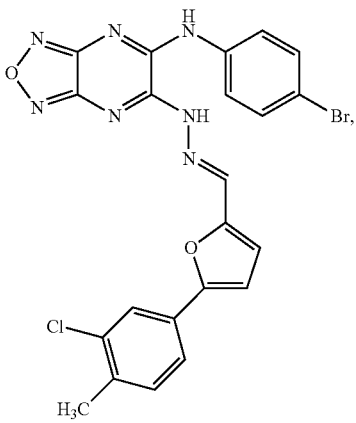

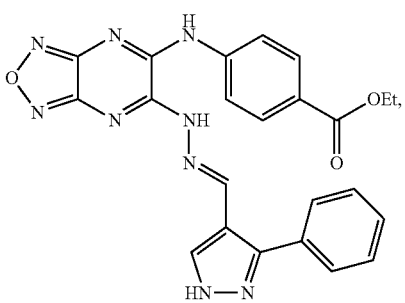

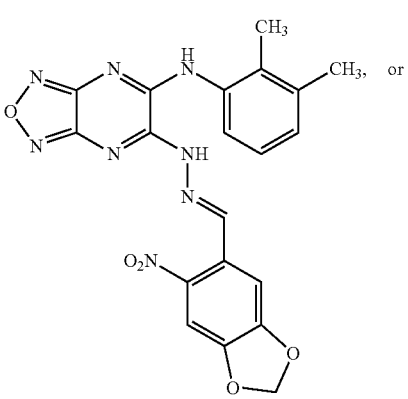

-continued

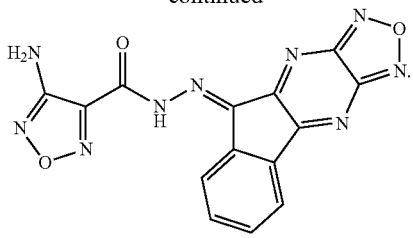

In some embodiments, wherein the survivin-targeting compound is:

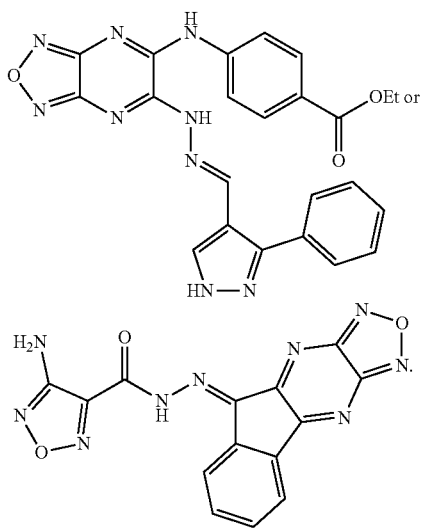

In some such embodiments, the survivin-targeting compound is:

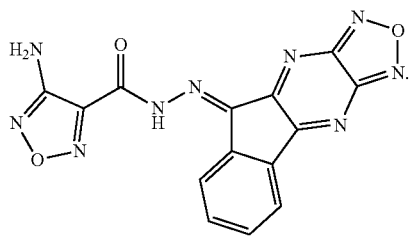 [SMILES: Nc1nonc1C(=O)N/N=C1\c2ccccc2-c2nc3nonc3nc21]

In some embodiments, the medicament is for treating breast cancer, colon cancer, lung cancer, pancreatic cancer, prostate cancer, ovarian cancer, or leukemia. In some such embodiments, the medicament is for treating prostate cancer.

In some embodiments, the medicament is designed to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

In a fifth aspect, this disclosure encompasses a method for identifying an anti-cancer compound. The method includes the step of performing in-silico screening of a library of compounds to identify one or more compounds in the library that would target critical hydrophobic core amino acid residues of the dimerization domain of an oncogenic dimeric protein.

In some embodiments, the method further includes the step of performing computational analysis to identify the critical hydrophobic core amino acid residues of the dimerization domain of the oncogenic dimeric protein.

In some embodiments, the method further includes the step of testing the one or more identified compounds for anti-cancer activity. In some such embodiments, this step is performed by contacting the one or more identified compounds with one or more cancer cells.

In some embodiments, the oncogenic dimeric protein is survivin.

Other objects, features and advantages of the disclosed compositions and methods will become apparent from the specification, claims and drawings.

BRIEF DESCRIPTION OF THE DRAWINGS

FIG. 3A shows non-denaturing PAGE analysis of compound effect on survivin dimerization. Purified survivin was incubated with different compounds followed by non-denaturing PAGE analysis of the protein and commassie blue staining.

FIG. 3B shows the chemical structure of LQZ-7.

FIGS. 3C and 3D show dose-dependent effect of LQZ-7 on survivin and 14-3-3σ dimerization as described in panel 3A.

FIG. 3E shows dose-dependent binding of LQZ-7 to survivin. The intrinsic fluorescence of LQZ-7 was measured in the absence or presence of survivin.

FIG. 3F shows non-denaturing PAGE analysis of nascent survivin. Survivin cRNA was used to program cell-free translation in rabbit reticulocyte lysate in the absence or presence of LQZ-7. [$^{35}$S]-labeled nascent proteins were subjected to non-denaturing PAGE and autoradiography analysis.

FIGS. 4A-4C show the effect of LQZ-7 on the expression of endogenous and ectopic survivin. DU145 cells were treated with LQZ-7 or DMSO vehicle control for different times followed by Western blot analysis of survivin (4A) or for 48 hrs for real-time RT-PCR analysis of survivin mRNA (4B). Panel 4C shows Western blot analysis of LQZ-7 effect on ectopic Flag-tagged survivin (F-survivin) in HEK293 cells.

FIGS. 4D-E show the effect of LQZ-7 of survivin stability and half-life. DU145 and PC-3 cells were pre-treated with cycloheximide (CHX) to inhibit protein synthesis followed by chasing for different times in the presence of LQZ-7 or DMSO control and Western blot analysis of remaining survivin. Panel E shows quantitation of survivin in panel D.

FIG. 4F shows that proteosome inhibitors MG132 and bortezomib reversed LQZ-7-induced survivin degradation. PC-3 cells were treated with LQZ-7 in the absence or presence of proteasome inhibitors followed by Western blot analysis of survivin.

FIG. 4G shows the effect of LQZ-7 on survivin synthesis. PC-3 cells were pulse labeled with [$^{35}$S]methionine in the absence or presence of LQZ-7. The newly synthesized survivin was immunoprecipitated, resolved on SDS-PAGE, and visualized by autoradiography.

FIG. 5A shows the chemical structures of LQZ-7 and its analogues.

FIG. 5B shows the effect of LQZ-7 and its analogues on PC-3 and DU145 cell survival as determined using MTT assay.

FIG. 5C shows the effect of LQZ-7 and its analogues on ectopic Flag-tagged survivin in HEK293 cells.

FIG. 5D shows the effect of LQZ-7F on endogenous survivin level in DU145 and PC3 cells.

FIG. 5E shows the effect of LQZ-7F on survivin stability. PC-3 cells were pre-treated with cycloheximide (CHX) to inhibit protein synthesis followed by chasing for different times in the presence of LQZ-7F or DMSO control and Western blot analysis of remaining survivin.

FIG. 5F shows the effect of proteasome inhibitors MG132 and bortezomib on LQZ-7F-induced survivin degradation.

FIG. 6A shows the IC$_{50}$ of LQZ-7F in human cell lines of different cancers as determined using MTT assay. 231, MDA-MB-231.

FIG. 6B shows the effect of LQZ-7F on human cancer cell survival as determined using colony formation assay.

FIGS. 6C and 6D show apoptosis assay. Cells were treated without or with different concentrations of LQZ-7F for 24 hrs followed by AnnexinV/PI dural staining and analysis of apoptotic cells using flow cytometry (6C) or subjected to Western blot analysis of cleaved PARP (6D).

FIGS. 6E-6F show Western blot and scatter plot analyses of survivin protein in different human cancer cell lines. Western blots were performed using 10 mg of protein from each total cell lysate. Scatter plot analysis of IC$_{50}$ and relative survivin protein level are shown for different cancer cell lines derived from six experiments.

FIGS. 8A-8B show the effect of LQZ-7F on ectopic xenograft tumor growth and body weight in male NSG mice. Arrow heads indicate treatments.

FIG. 8C shows the gross anatomy of xenograft tumors.

FIG. 8D shows the final wet weight of xenograft tumors.

FIGS. 8E-8F show immunohistochemistry (8E) and Western blot (8F) analyses of survivin in xenograft tumors.

DETAILED DESCRIPTION

A. In General

Figure 1A:
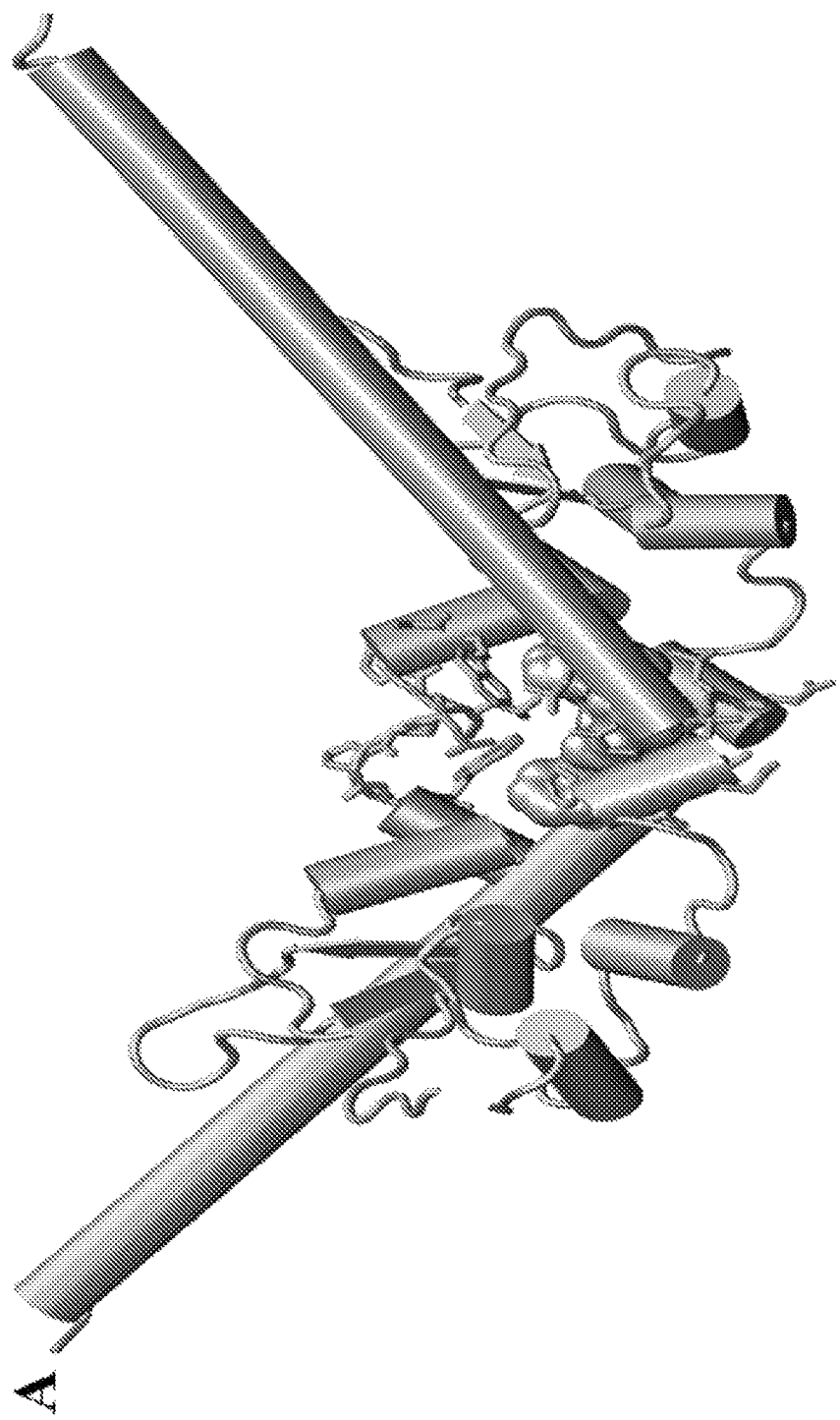
FIG. 1A shows the overall structure of survivin dimer. The two subunits shown in ribbon are colored in cyan and orange, respectively. Interfacial non-core residues shown in stick representation are colored green. The deeply buried dimerization core is represented by their molecular surface in gray.

This invention is not limited to the particular methodology, protocols, cell lines and reagents described, as these may vary. The terminology used herein is for the purpose of describing particular embodiments only, and is not intended to limit the scope of the present invention, which will be limited only by the appended claims.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The present invention encompasses the use of any optically-active, racemic, polymorphic, or stereroisomeric form, or mixtures thereof, which form possesses properties useful in the treatment of tumor-related conditions described and claimed herein.

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, such as, sodium hydroxide. Also, esters of the phenolic compounds can be made with aliphatic and aromatic carboxylic acids, such as for example, acetic acid and benzoic acid esters. As used herein, the term "pharmaceutically acceptable salt" refers to a compound formulated from a base compound which achieves substantially the same pharmaceutical effect as the base compound.

In addition, this invention further includes methods utilizing hydrates of the anti-tumor compounds. The term "hydrate" includes but is not limited to hemihydrates, monohydrates, dihydrates, trihydrates and the like.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor compounds. As used herein, administration can be accomplished in vitro, i.e., in a test tube, or in vivo, i.e., in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor compound; or (2) is susceptible to a disorder that is preventable by administering the anti-tumor compound.

As used herein, "pharmaceutical composition" means therapeutically effective amounts of the anti-tumor compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. The optimum effective amounts can be readily determined by one of ordinary skill in the art using routine experimentation.

Pharmaceutical compositions are liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms, protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1M and preferably a 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Katre et al., 1987; Newmark et al., 1982). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, 1987; Buchwald et al., 1980; Saudek et al., 1989). In another embodiment, polymeric materials can be used. In yet another embodiment, a controlled release system can be placed in proximity to the therapeutic target, i.e., the skin, thus requiring only a fraction of the systemic dose (see, e.g., Goodson, 1984). Other controlled release systems are discussed in the review by Langer, 1990.

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a subject by, for example, subcutaneous implantation of a pellet. In a further embodiment, a pellet provides for controlled release of anti-tumor compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating or tablet-forming processes. For oral administration, the anti-tumor compounds or their physiologically tolerated derivatives such as salts, esters, N-oxides and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin; with disintegrating agents such as cornstarch, potato starch, alginic acid; or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the anti-tumor compounds or their physiologically tolerated derivatives such as salts, esters, N-oxides and the like are converted into a solution, suspension, or expulsion, if desired, with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, such as for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer 1990; Treat et al., 1989; Lopez-Berestein ibid.; see generally ibid).

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as, for example, hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In sum, the present invention provides numerous methods and pharmaceutical compositions for the treatment, inhibition, recurrence and occurrence of cancer or cancer related conditions, including without limitation leukemia, prostate cancer, breast cancer, colon cancer, lung cancer, pancreatic cancer or ovarian cancer.

The following Example is offered by way of illustration only, and not by way of limitation.

Example: Identifying Anti-Cancer Compounds that Target the Dimerization Interface of Survivin for Degradation Many ideal oncogenic protein targets are considered "undruggable" due to lack of known enzymatic activities. Survivin, a member of the IAP family, is such a protein and exists as a homo-dimer.

In this Example, we tested the hypothesis that a compound that binds to the interfacial surface may inhibit survivin dimerization, promote survivin degradation, and lead to spontaneous apoptosis. By combining computational analysis of the dimerization interface of survivin and in-silico screening targeting the interface, we successfully identified a hit compound that induces proteasome-dependent survivin degradation. Further analysis of its analogues helped identify a potential lead candidate (LQZ-7F) that is effective in inhibiting survival of multiple cancer cell lines with $IC_{50}$ of 0.4-4.4 µM. LQZ-7F is also effective in inducing survivin degradation, spontaneous apoptosis, mitotic arrest, and in suppressing xenograft tumor growth. Together, we conclude that combining computational analysis of dimerization interface and in-silico screening targeting targeting critical hydrophobic core residues in the interface is a viable approach to target "undruggable" ongogenic dimeric proteins for anticancer drug discovery.

Introduction

It is known that exposure of the hydrophobic interface of a dimeric protein often leads to conformational change[24,25], which causes destabilization and degradation of the protein by proteosome or autophagy[26,27]. Because survivin exists as a homo-dimer, we hypothesized that a small molecule compound that inhibits survivin dimerization may promote survivin degradation via proteasome and eliminate the protein, leading to spontaneous apoptosis. We recently developed a novel strategy to identify interfacial hydrophobic core units critical for homo-dimerization[28,29]. Using this strategy, we tested the above hypothesis by first identifying the hydrophobic core residues critical for survivin dimerization followed by in-silico screening for inhibitors targeting the critical core residues, as well as in vitro and cell-based assays. We identified a hit compound, LQZ-7, which dissociated dimeric survivin and induced survivin degradation in a proteasome-dependent manner. Further analysis identified several analogues of the hit compound, which resulted in a potential lead compound (LQZ-7F) that inhibits survival of multiple cancer cell lines with submicromolar $IC_{50}$, suppresses xenograft tumor growth, and inhibit survivin in vivo.

Results

Analysis of Dimerization Domain of Survivin.

To effectively target the dimerization domain of survivin, we first analyzed the dimerization domain to identify residues that are critical for survivin dimerization as target for in-silico screening. The interacting residues between the two identical subunits are comprised of residues 6-10, 93-99 and 101-102 (6L, 7P, 8P, 9A, 10W, 93F, 94E, 95E, 96L, 97T, 98L, 99G, 101F, 102L). About 80% of these residues are hydrophobic, which is comparably high considering the average of non-polar interaction is only ~50% in dimeric proteins[1]. The dimeric survivin has a total calculated solvent accessible area of 18,039 Å$^2$. The buried accessible area in the dimeric interface of a monomeric survivin is 550 Å$^2$ and it occupies only 6% of the total accessible area of a monomer (9,044 Å$^2$), which is much less than the average value (~20%) in dimeric or oligomeric proteins[1,2,3]. The relatively small area and the high hydrophobicity of the interactive surface indicate that it may be a good target site for drug discovery.

Figure 1B:
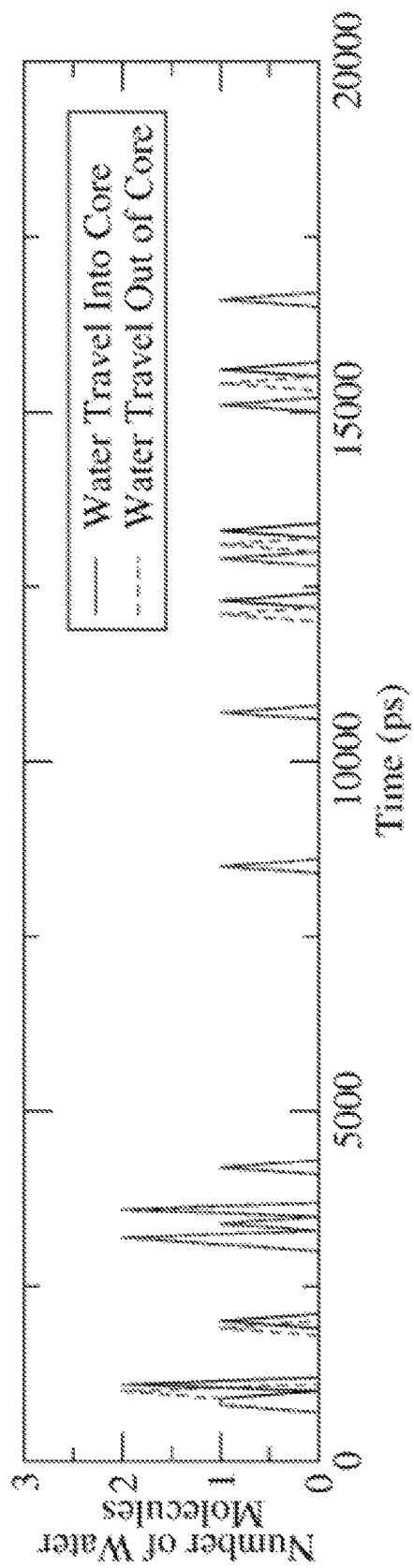
FIG. 1B is a graph showing the water molecules exchanged in the survivin dimerization core unit from MD simulation.

Previously, we found that dimeric proteins may have dimerization core units that are sealed from water penetration and are critical for homo-dimerization[28]. Survivin has one dimerization core unit consisting of four residues, Leu$^{98}$ and Phe$^{101}$ from one subunit and the same residues from another subunit (FIG. 1A). Water exchange rate in this dimerization core unit was determined by performing 20-ns water explicit MD simulation and a computational method developed by us previously[28]. As shown in FIG. 1B, few water molecules moved in or out the dimerization core during the 20-ns simulation with an estimated water exchange rate at 0.5 water/200 ps, which is comparable with that of the 14-3-3σ dimerization core[28]. It is, however, significantly lower than that of the mutant 14-3-3σ molecule that lost dimerization activity and has a much higher water exchange rate (>4 water/200 ps). These findings suggest that the dimerization core unit of survivin consisting of Leu$^{98}$ and Phe$^{101}$ is tightly sealed and may be critical for the formation of stable survivin dimers. Disrupting this core formation may affect survivin dimerization. Indeed, mutation of Phe$^{101}$ to Ala$^{101}$ together with Leu$^{102}$ to Ala$^{102}$ mutation has shown to disrupt survivin dimerization[30].

Identification of LQZ-7 Targeting the Dimerization Domain of Survivin.

Figure 2:
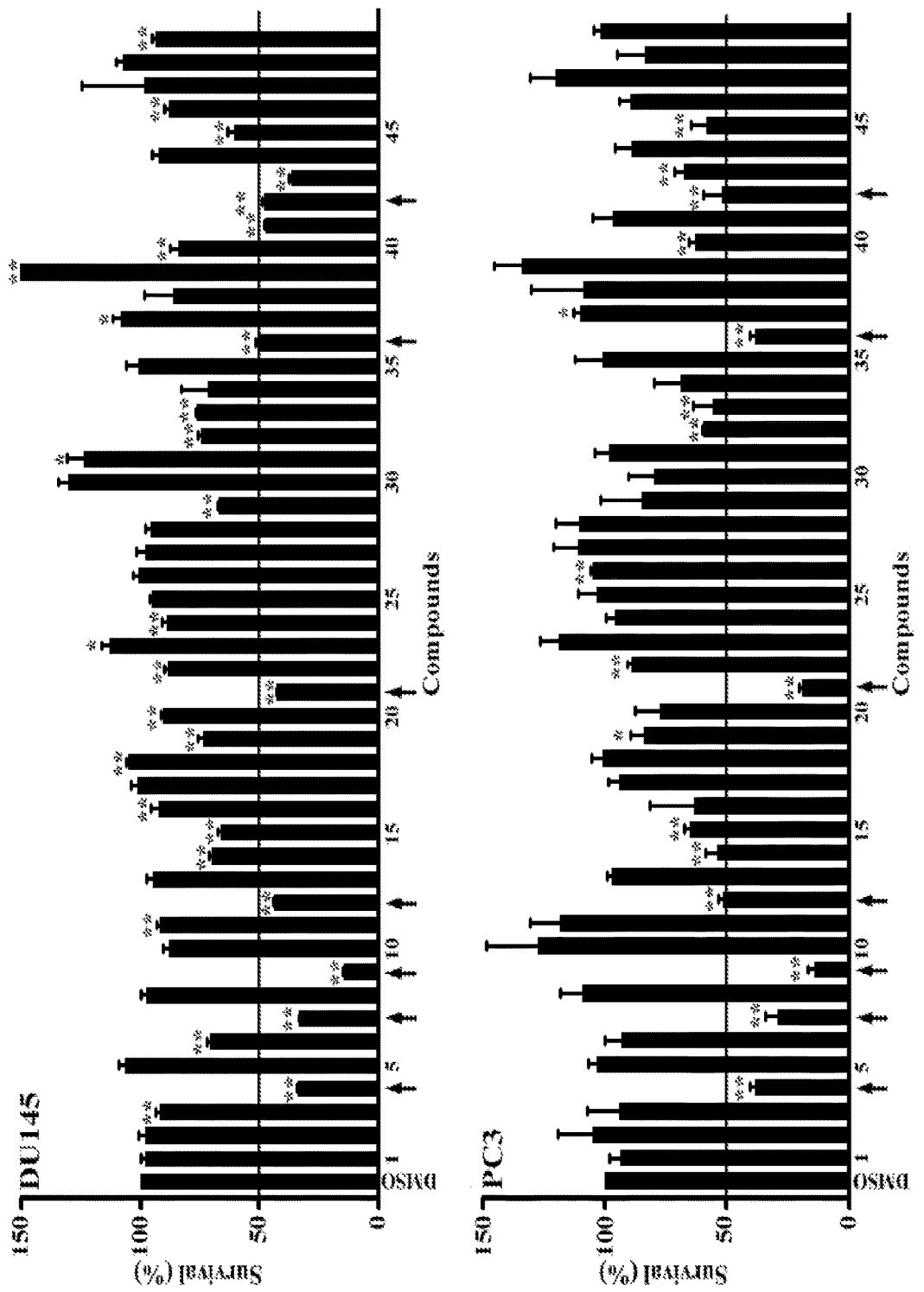
FIG. 2 shows the effect of compounds from in-silico screening on cancer cell survival. Human prostate cancer cell lines DU145 (top) and PC3 cells (bottom) were cultured in the presence of vehicle DMSO or 20 μM compounds off in-silico screening for 3 days followed by MTT assay. Cells survived in the presence of various compounds were normalized to that treated by DMSO vehicle. Arrows indicate compounds that inhibited >50% in cell survival. (*$p<0.05$; **$p<0.01$).

To identify small molecule compounds that can potentially inhibit survivin dimerization, we performed in-silico screening of ~200,000 compounds targeting the critical hydrophobic core residues Leu$^{98}$ and Phe$^{101}$ in the dimeric interface using DOCK. Of 100 top-scoring compounds of diversified structures, 49 chemical samples were commercially available and tested for their cytotoxicity using two human cancer cell lines DU145 and PC-3. As shown in FIG. 2, only compounds 4, 7, 9, 12, 21, 36, and 42 at 20 µM were able to inhibit ≥50% survival of both DU145 and PC-3 cells. Consequently, these compounds were chosen for further investigation.

Figures 3A, 3B, 3C, 3D:
FIGS. 3A-3F. Identification and characterization of LQZ-7.
Figures 3E, 3F:
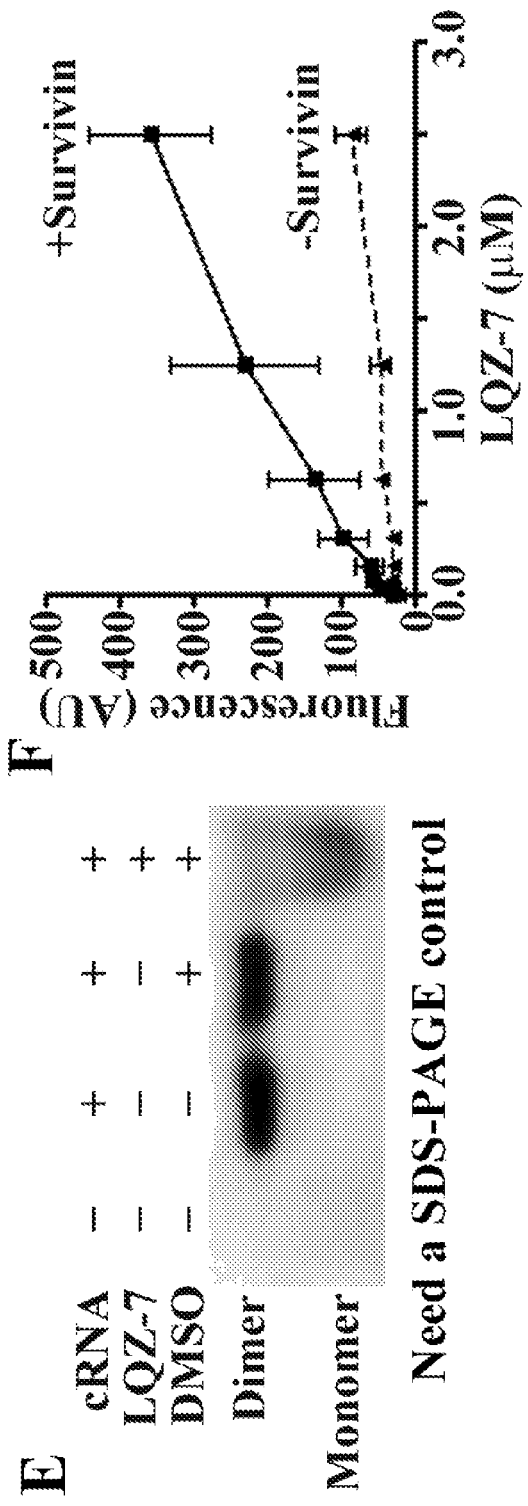

The selected compounds were first tested for their ability to dissociate survivin dimers using purified survivin and non-denaturing PAGE analysis. As shown in FIG. 3A, compound #7 (named LQZ-7 with structure shown in FIG. 3B) was able to affect the mobility of purified survivin, presumably by dissociating the dimeric survivin into monomers. To confirm its activity and test its potential selectivity, we had LQZ-7 resynthesized and performed a dose-response analysis of its activity in dissociating dimeric survivin and an irrelevant control but similar dimeric protein, 14-3-3σ. Although 100 µM of LQZ-7 appears to be required to completely dissociate dimeric survivin (FIG. 3C), LQZ-7 at 100 µM had no effect on 14-3-3σ dimerization (FIG. 3D). We also performed non-denaturing PAGE analysis of nascent proteins synthesized in cell free system in the presence of LQZ-7. As shown in FIG. 3E, 20 µM of LQZ-7 achieved a complete inhibition of survivin dimerization. Together, these findings suggest that LQZ-7F can inhibit dimerization of nascent survivin and dissociate dimeric survivin with selectivity over other homo-dimeric proteins such as 14-3-3σ. Less LQZ-7 is required to inhibit dimerization of nascent survivin than dissociating dimeric survivin also suggests that inhibiting dimerization of newly synthesized proteins is dynamically easier than dissociating the existing dimeric proteins.

To verify that LQZ-7 indeed binds to survivin and inhibit survivin dimerization, we took advantage of the intrinsic fluorescent property of LQZ-7 and performed a fluorogenic titration assay in the presence or absence of survivin as previously described[31]. FIG. 3F shows that the intrinsic fluorescence of LQZ-7 dramatically increases in the presence of recombinant survivin, indicating that LQZ-7 likely interacts with survivin. The $K_d$ of LQZ-7 binding to survivin is estimated to be 0.24±0.11 µM.

LQZ-7 Accelerates Proteasome-Dependent Degradation of Endogenous Survivin.

Figures 4A, 4B, 4C:
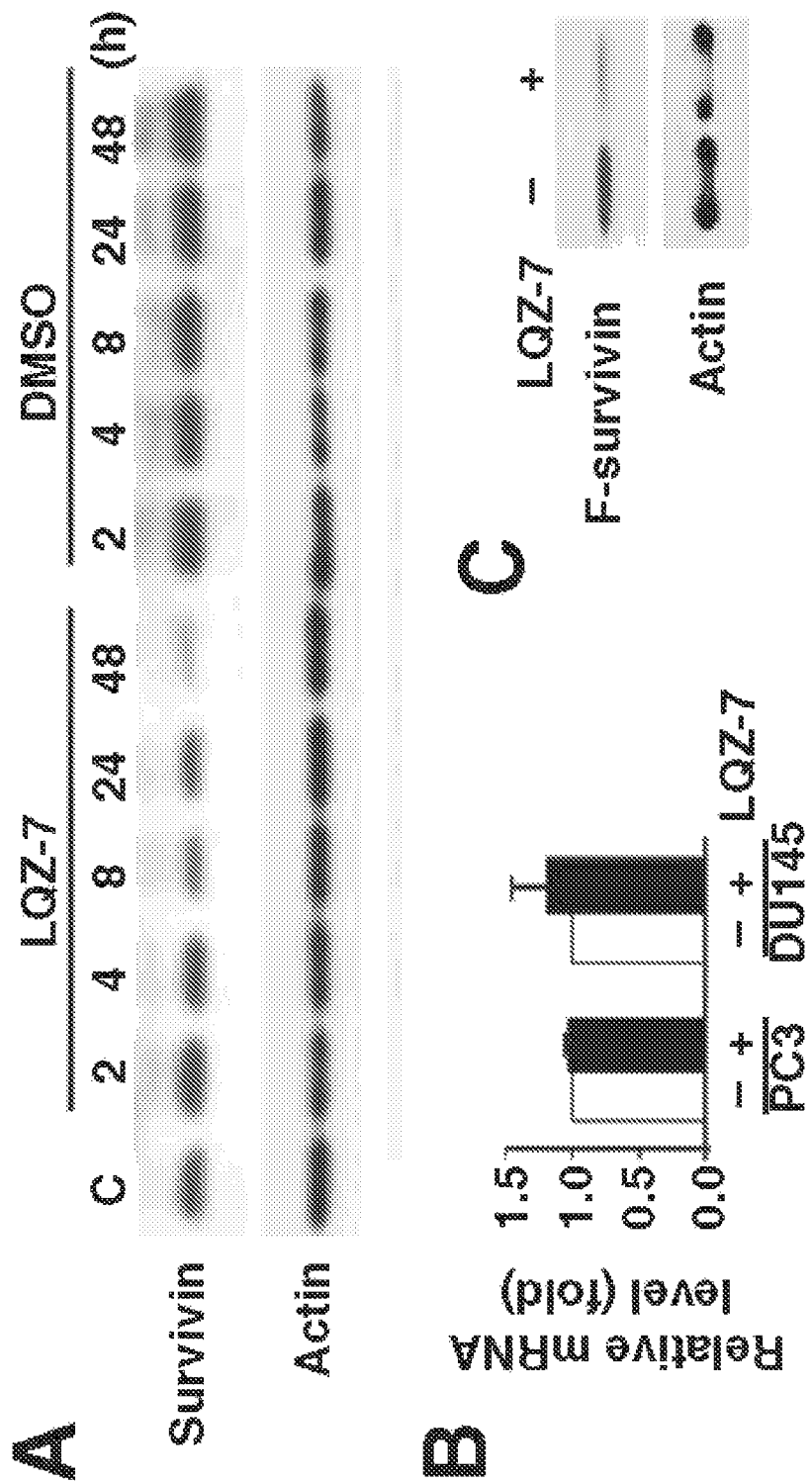
FIGS. 4A-4G show that LQZ-7 induces proteasome-dependent survivin degradation.

Exposure of hydrophobic interface of a dimeric protein often leads to conformational change[24,25], which causes destabilization and degradation of the protein by proteasome or autophagy[26,27]. We, thus, hypothesized that LQZ-7 may cause proteasome-dependent degradation of survivin by dissociating survivin dimers and exposing the hydrophobic dimeric interface. To test this hypothesis, we first treated DU145 cells with LQZ-7 for different times followed by determination of endogenous survivin using Western blot analysis. FIG. 4A shows that LQZ-7 treatment indeed reduced survivin protein level compared with vehicle control treatment. Similar results were also observed with PC-3 cells (data not shown). However, LQZ-7 treatment had no effect on the level of survivin mRNA as determined using real time RT-PCR (FIG. 4B). LQZ-7 treatment also effectively reduced the level of ectopic HA-tagged survivin in HEK293 cells under the control of CMV promoter (FIG. 4C). These observations together suggest that survivin loss induced by LQZ-7 is likely at the protein but not mRNA level.

Figure 4D:
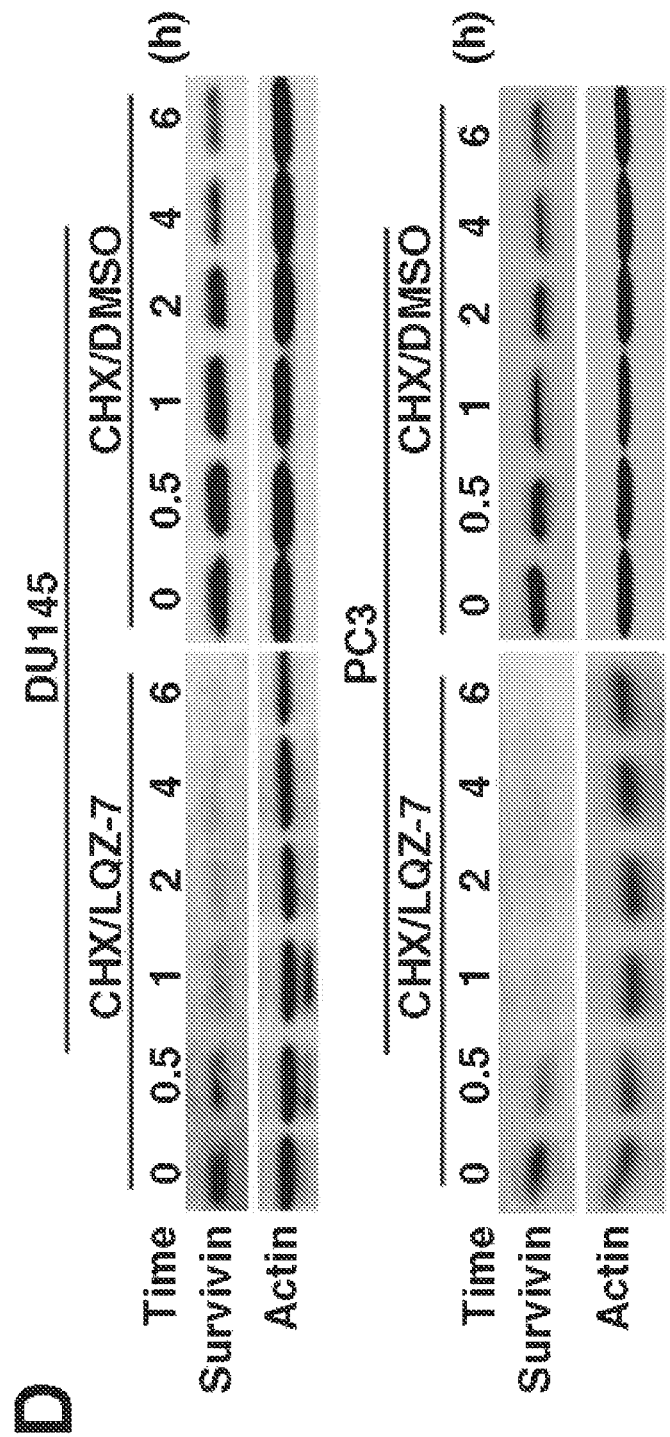
Figures 4E, 4F, 4G:
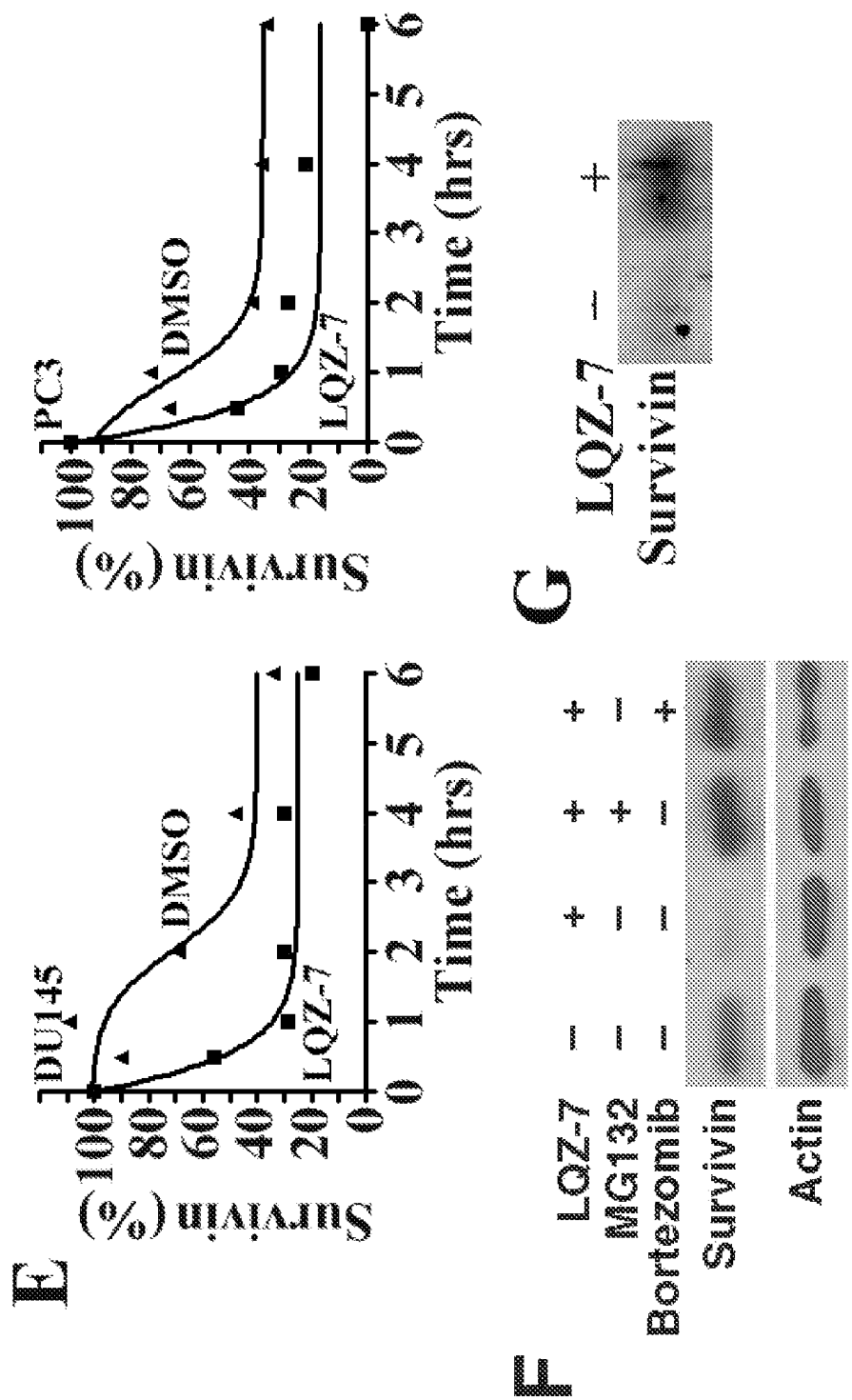

We next determined if LQZ-7 causes survivin degradation by examining its effect on survivin half-life. For this purpose, DU145 and PC-3 cells were pre-treated with cycloheximide to inhibit synthesis of new proteins followed by treatment with LQZ-7 for different times. FIGS. 4D-E show that the half-life of survivin is ~1.5-2.5 hrs in control-treated DU145 and PC-3 cells, consistent with previously reported survivin half-life[32,33] However, following LQZ-7 treatment the half-life of survivin was reduced to ~30 min. Co-treatment with a proteasome inhibitor, MG132, reversed LQZ-7-induced survivin loss (FIG. 4F), consistent with previous report that survivin degradation is mediated by proteasome[34]. We also found that LQZ-7 does not inhibit survivin protein synthesis as determined using [$^{35}$S]methionine pulse-labeling in combination with immunoprecipitation of survivin following LQZ-7 treatment (FIG. 4G). Together, the above findings suggest that LQZ-7 causes proteasome-dependent survivin degradation possibly by inhibiting dimerization and exposing the hydrophobic core residues of survivin.

Characterization of LQZ-7 Analogues.

Figure 5A:
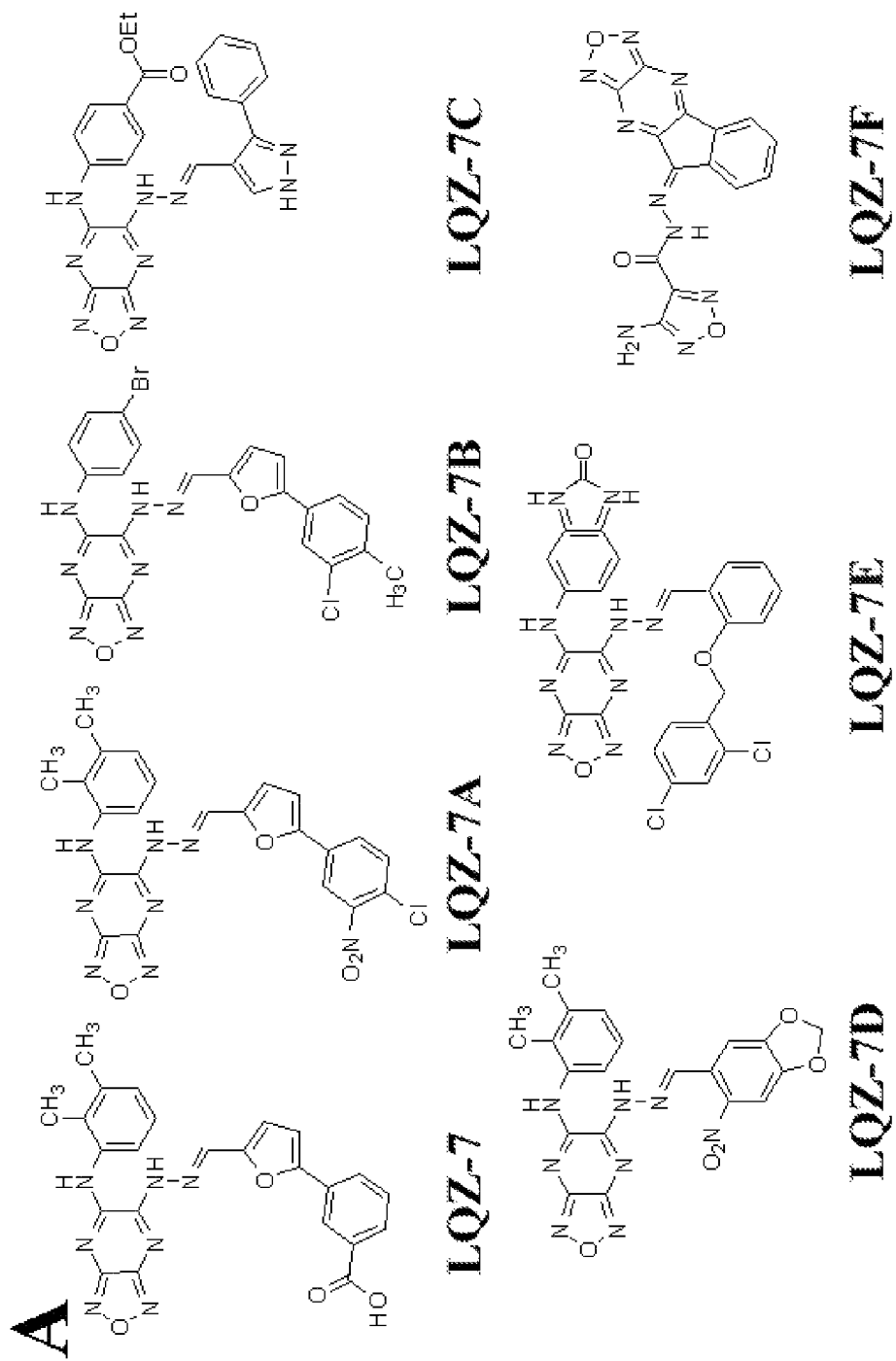
FIGS. 5A-5F show the characterization of LQZ-7 analogues.
Figures 5B, 5C:
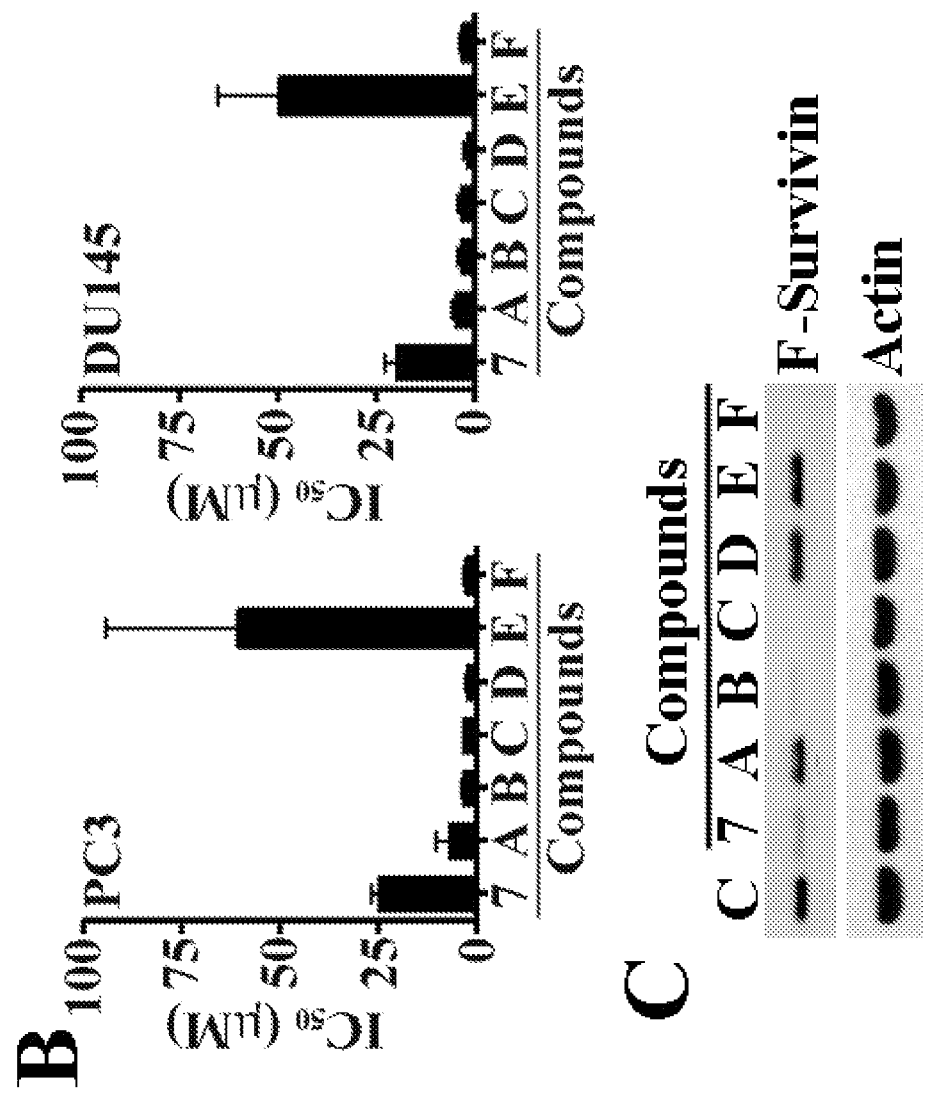

Although LQZ-7 dissociates survivin dimer in vitro and causes survivin degradation in cells, cell-based cytotoxicity assays showed that the $IC_{50}$ of LQZ-7 in human PC3 and DU145 cells was approximately 25 mmol/L (FIG. 5B). The modest IC50 may be due to the possibility that the carboxyl group in LQZ-7 (FIG. 5A) impedes its cellular permeability. To improve cellular effect of LQZ-7, we searched the SPECS database and identified six commercially available analogues (LQZ-7A, B, C, D, E, and F; FIG. 5A). The chemical samples of these analogues were obtained and tested first for their cytotoxicity to DU145 and PC3 cells compared with the initial hit LQZ-7. FIG. 5B shows that five of the six analogues have much lower $IC_{50}$ than LQZ-7 for both cells. These analogues together with LQZ-7 were then used to test their effect on the expression of ectopic Flag-tagged survivin in HEK293 cells. As shown in FIG. 5C, although LQZ-7A, D, and E had no effect on the level of Flag-tagged survivin, LQZ-7B, C, and F all reduced survivin protein level. It appears that LQZ-7C and F completely eliminated survivin whereas the parent compound LQZ-7 did not, consistent with their lower $IC_{50}$ than the parent compound. The fact that LQZ-7E has high $IC_{50}$ and does not reduce surviving protein suggests that LQZ-7E may not bind to and inhibit survivin. It remains unknown why LQZ-7A and D have no effect on survivin level while maintaining low $IC_{50}$.

Figures 5D, 5E, 5F, 5G:
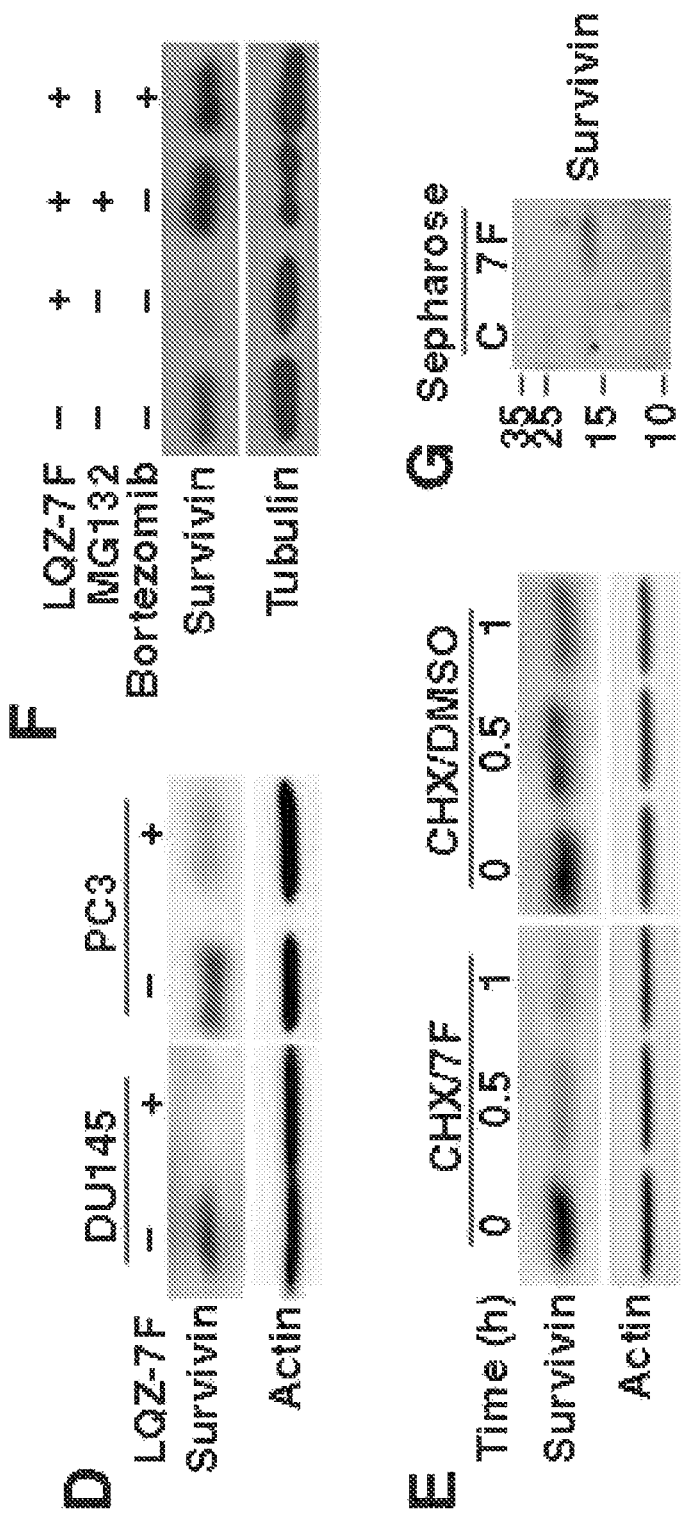
FIG. 5G shows a pull-down assay. LQZ-7F was immobilized onto CNBr-activated Sepharose and used to pull down recombinant survivin, followed by separation on SDS-PAGE and silver staining.

Of the two analogous compounds (LQZ-7C and F) that have the best $IC_{50}$ and ability to eliminate survivin, LQZ-7F is unique, smaller, and simpler in structure with a primary amine group as an advantage for further study. Thus, we elected to pursue LQZ-7F further as a potential lead and tested its activity in suppressing the expression and inducing degradation of endogenous survivin. Similar to LQZ-7, LQZ-7F effectively suppressed endogenous survivin expression in both DU145 and PC3 cells (FIG. 5D) and increased degradation of endogenous survivin (FIG. 5E). Furthermore, proteasome inhibitors MG132 and bortezomib both were able to rescue LQZ-7F-induced survivin degradation (FIG. 5F). Thus, LQZ-7F, similar as its parent compound LQZ-7, also induces survivin degradation in a proteasome dependent manner.

Figure 5H:
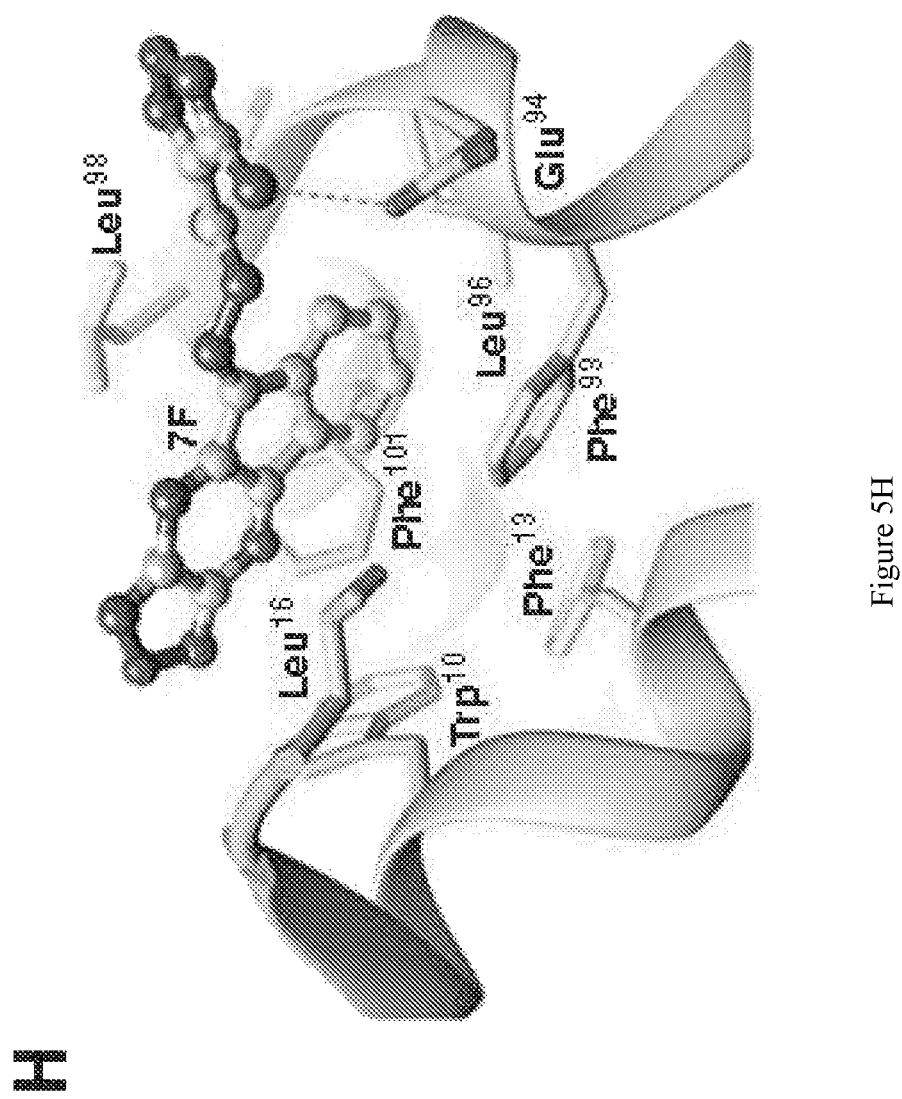
FIG. 5H shows the predicted binding mode of LQZ-7F (stick and ball) in survivin (ribbon) using DOCK.

LQZ-7F Interaction with Survivin:

To investigate if LQZ-7F indeed binds to survivin, we took advantage of the primary amine group and immobilized LQZ-7F onto CNBr-activated sepharose for a pull-down assay using purified survivin. As shown in FIG. 5G, survivin was successfully pulled down by sepharose-immobilized LQZ-7F, but not by the control beads without LQZ-7F. Thus, LQZ-7F, similar to LQZ-7, may bind directly to survivin. To understand how LQZ-7F interacts with survivin, we performed docking analysis of LQZ-7F in the dimerization interface of survivin, which revealed two key interactions between LQZ-7F and survivin: (a) H-bond between the primary amine group of LQZ-7F and Glu[94] of survivin; (b) π-π stacking and hydrophobic interaction between the tetracyclic furazanopyrazine ring of LQZ-7F and the hydrophobic residues Trp[10] and Phe[93] in addition to the dimerization core residues Leu[98] and Phe[101] (FIG. 5H).

LQZ-7F Inhibits Survival of Multiple Cancer Cell Lines by Inducing Apoptosis.

Figures 6A, 6B, 6C, 6D:
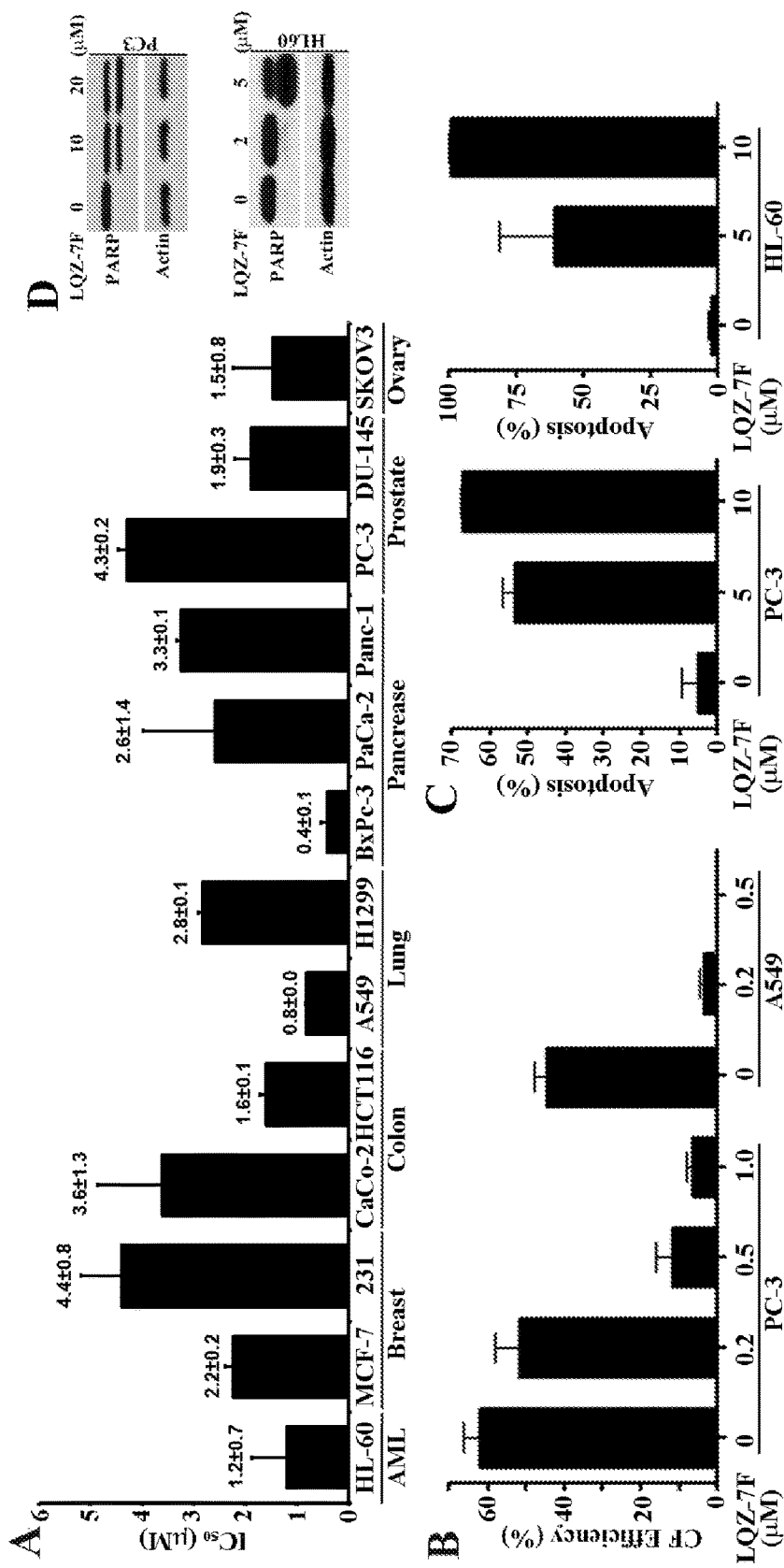
FIGS. 6A-6F show the effect of LQZ-7F on cancer cell survival.

Survivin is ubiquitously up-regulated in human cancers and, thus, inhibiting survivin may be a general approach to help eradicate many cancers. Toward this goal, we tested the effect of LQZ-7F on survival of multiple human cancer cell lines representing acute myeloid leukemia and cancers of breast, colon, lung, pancreas, prostate, and ovary using MTT assay. As shown in FIG. 6A, LQZ-7F effectively inhibited survival of all cancer cell lines with $IC_{50}$ ranging between 0.4-4.4 μM.

The activity of LQZ-7F in suppressing cancer cell survival was further evaluated using colony formation assay for PC3 and A549 cells. As shown in FIG. 6B, the colony formation efficiency of PC3 cells was reduced from approximately 62% of the control to approximately 52, 12, and 8% following treatments with LQZ-7F at 0.2, 0.5, and 1 mmol/L, respectively. A549 cells were more sensitive to LQZ-7F with lower $IC_{50}$ than PC3 cells and the colony formation efficiency were consistently reduced more from 45% of the control treatment to approximately 2.5% and 0% treated by 0.2 and 0.5 mmol/L of LQZ-7F, respectively.

Previously, it has been shown that dominant negative survivin causes spontaneous apoptosis of PC3, DU145, and LNCaP cells (12). We next tested if LQZ-7F also causes spontaneous apoptosis by inhibiting survivin as determined by Annexin V staining. For this experiment, we tested PC3 and HL-60 as representative cells because PC3 has high whereas HL-60 has intermediate $IC_{50}$ against LQZ-7F (FIG. 6A). As shown in FIG. 6C, 54% to 69% apoptosis for PC3 and 66% to 98% apoptosis for HL-60 cells were generated following treatments with 5 to 10 mmol/L LQZ-7F. These findings were further validated by determining the cleavage of PARP-1, a substrate of caspases during execution of apoptosis, in both PC3 and HL-60 cells following LQZ-7F treatments (FIG. 6D).

Figure 6E:
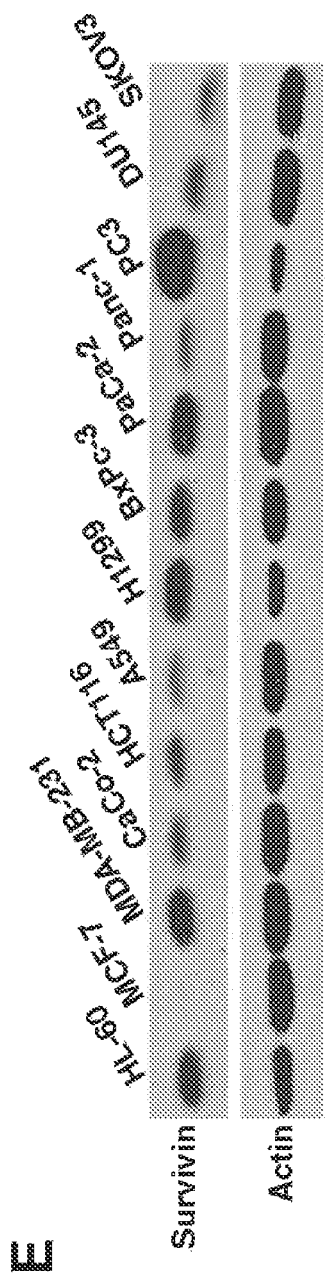
Figure 6F:
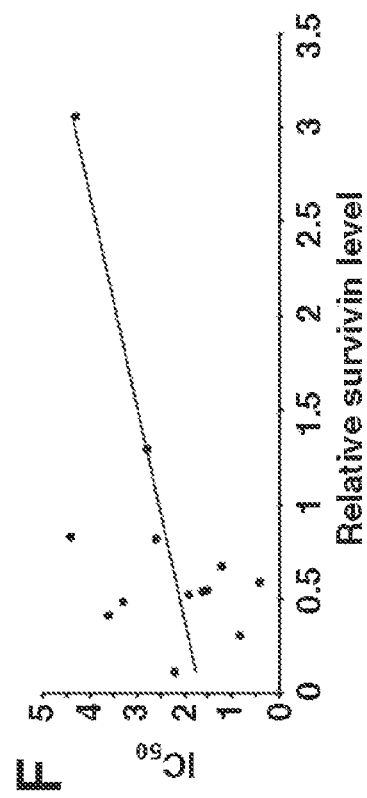

Finally, we tested survivin expression in all 13 cell lines (FIG. 6E) and performed a correlation analysis between survivin level and $IC_{50}$. As shown in FIG. 6F, the $IC_{50}$ values strongly associate with survivin protein level in these cells with a Pearson correlation coefficient of 0.52, indicating that LQZ-7F may suppress the survival of these cancer cells by acting on survivin.

LQZ-7F Treatments Disrupt Microtubule Structure and Cause Mitotic Arrest.

Figure 7:
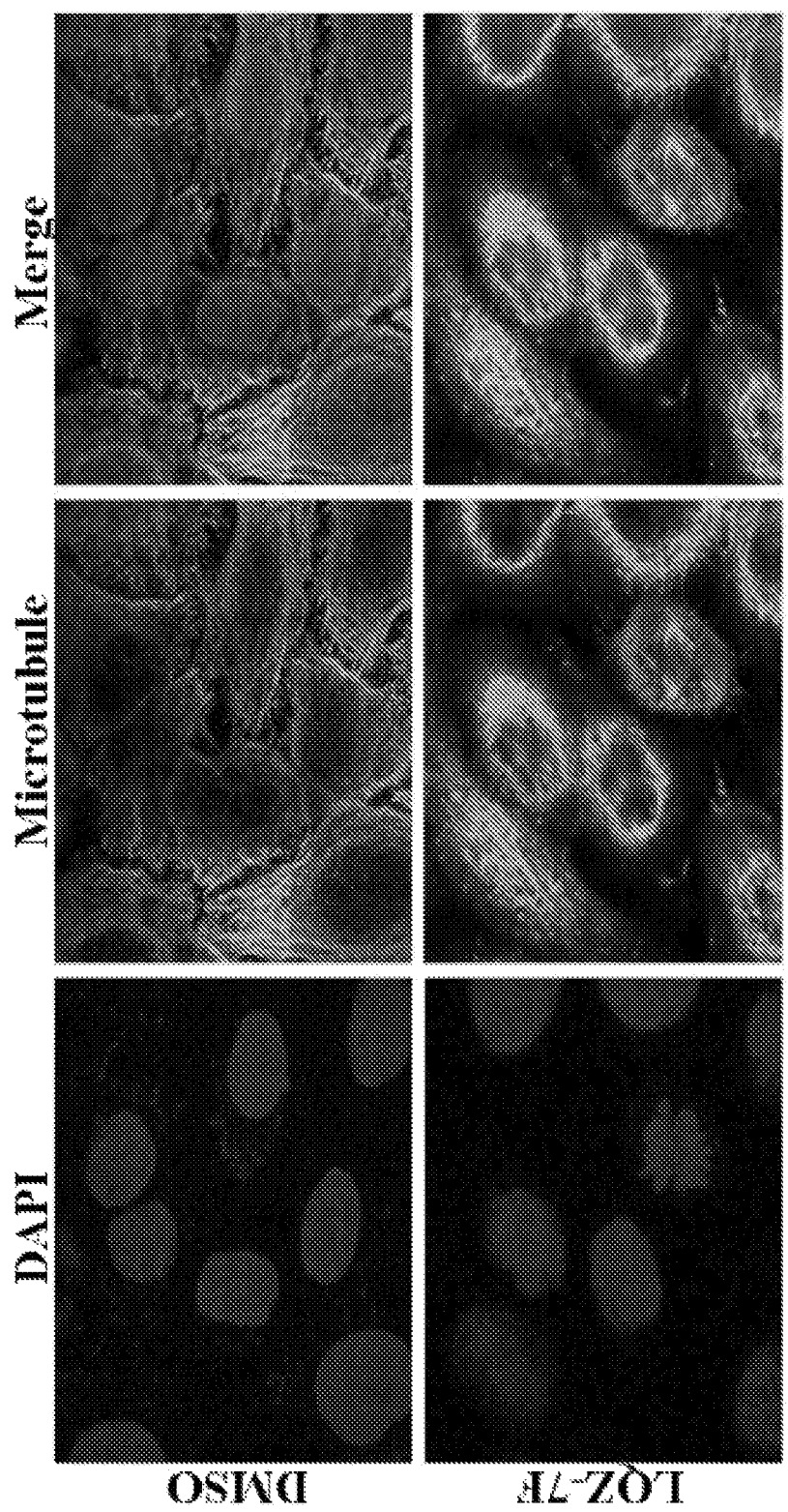
FIG. 7 shows the effect of LQZ-7F on microtubule structure. PC3 cells were treated without or with 2 μM LQZ-7F for 24 hours followed by immunostaining of α-tubulin and counter-stained with DAPI. The images were captured using confocal microscopy.

Survivin has been shown to have dual functions in inhibiting apoptosis and in promoting cell cycle progression[1]. The later was thought to derive from survivin action in destabilizing microtubules both in vitro and in vivo[35,36]. Thus, to further determine LQZ-7F effect on survivin, we analyzed microtubule structure following LQZ-7F treatment in PC-3 cells. As shown in FIG. 7A, the control DMSO-treated cells have orderly microtubule fibers in all cells. However, the microtubule structure was severely disrupted following LQZ-7F treatments. It also appears that many cells are arrested in mitotic phase with aberrant spindles following LQZ-7F treatments. These observations are consistent with the role of survivin in microtubule dynamics[37,38] and as a subunit of the chromosomal passenger complex that is essential for proper chromosome segregation and cytokinesis[39,40].

LQZ-7F Inhibits Growth of Xenograft Tumors by Inhibiting Survivin.

Figures 8A, 8B:
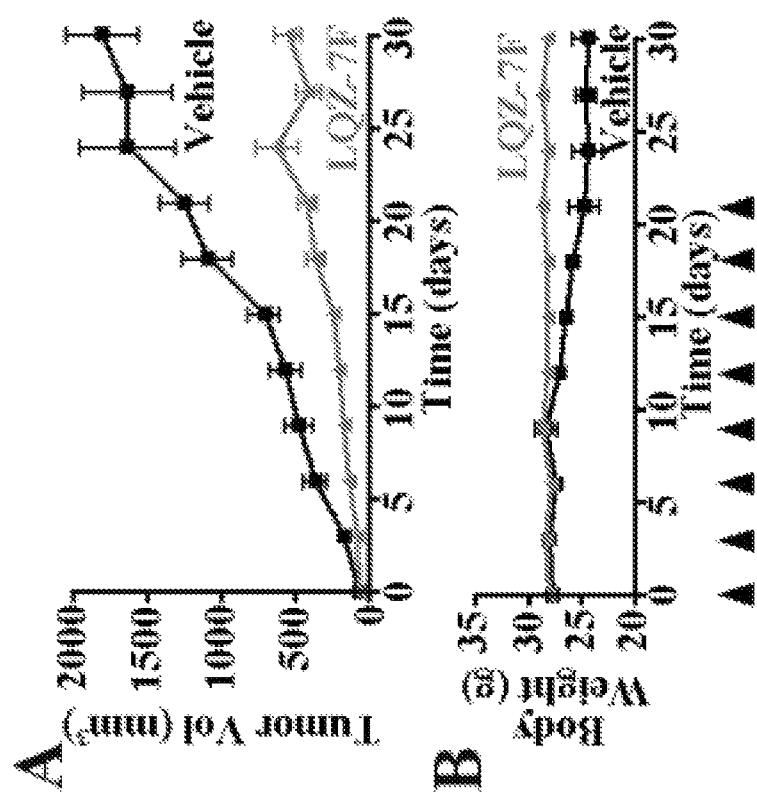
FIGS. 8A-8F show in vivo efficacy of LQZ-7F.

We next determined if LQZ-7F is active in suppressing tumor growth in vivo using xenograft animal model. For this purpose, NOD/SCID mice were first implanted subcutaneously with PC-3 cells to establish xenograft tumors. PC-3 cell was chosen because it has highest $IC_{50}$ (FIG. 6). When the xenograft tumor reached the size of ~100 mm$^3$, the mice were randomized into two groups and treated with 25 mg/kg LQZ-7F or vehicle control via IP injection once every three days for total of 8 treatments. The growth of the xenograft tumors were measured using a caliper and body weight was monitored every three days for a total of 30 days. As shown in FIG. 8A, the growth of xenograft tumors was significantly inhibited in the LQZ-7F-treated group compared to the tumors in vehicle control-treated group. However, the body weight of mice in the treatment group remained constant after multiple dosing (FIG. 8B), indicating that LQZ-7F may not cause major toxicity after multiple dosing. In fact, the body weight of the control group dropped slightly possibly due to disease burden of xenograft tumors. This symptom appears to be alleviated by LQZ-7F treatment, consistent with smaller tumor size in the treatment group.

Figures 8C, 8D, 8E, 8F:
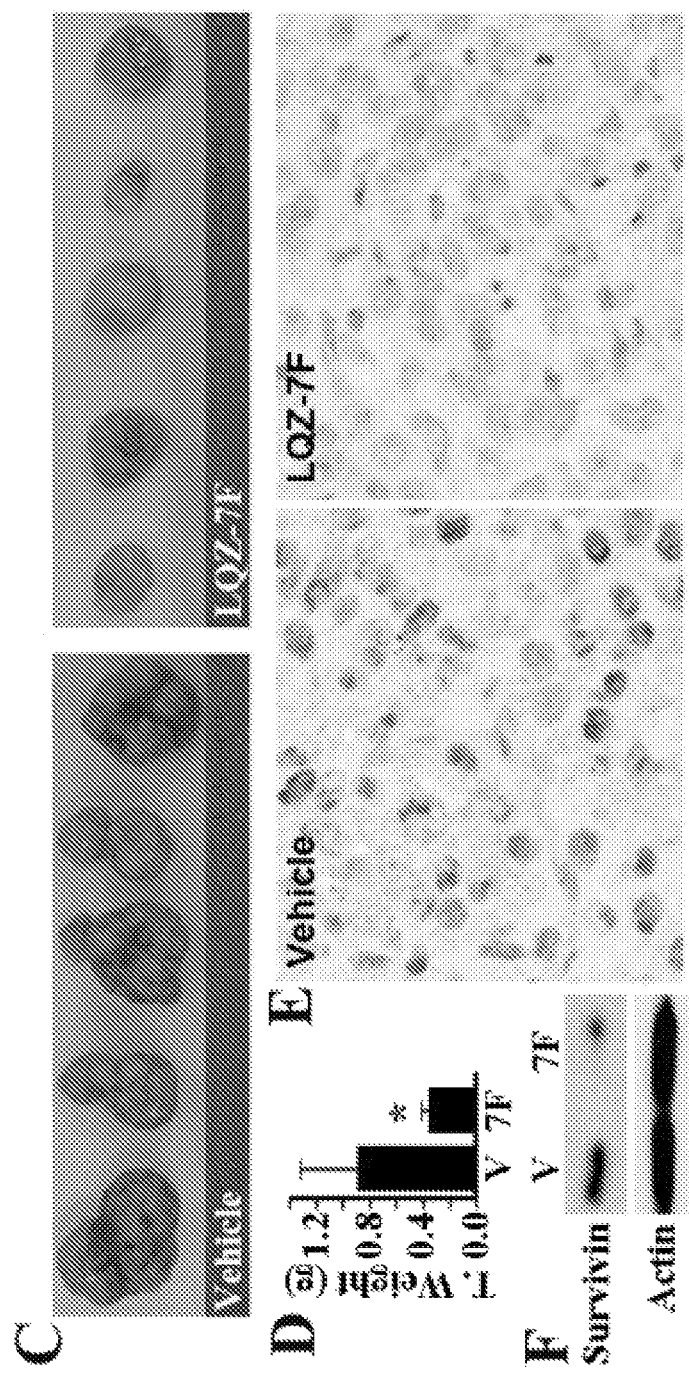

The final dissected tumors in the treatment group appear to be small and round with smooth surface whereas the tumors of the control group appear to be irregular and bigger (FIG. 8C), suggesting that the tumors in treatment group are confined whereas the tumors in the control group are aggressive. The average weight of the tumors in the treatment group is significantly less than that in the control group (FIG. 8D). The LQZ-7F-treated tumors also appear to have more apoptotic cells than the control-treated tumors (FIG. 8E). Western blot and IHC staining analyses showed that survivin in xenograft tumors of the LQZ-7F-treated group was dramatically reduced compared with the tumors of the control-treated group, suggesting that the effect of LQZ-7F on xenograft tumor growth may be due to its binding to survivin and induction of survivin degradation in vivo.

Discussion

In this Example, using in-silico screening targeting the critical hydrophobic core residues in dimeric interface following detailed analysis of the buried surface area, we successfully identified a potential lead inhibitor (LQZ-7F) that can bind directly to survivin and cause proteasome-dependent survivin degradation. LQZ-7F has an $IC_{50}$ of 0.4-4.4 µM against multiple cell lines of different human cancers and induces spontaneous apoptosis. It is also effective in suppressing xenograft tumor growth and reduces survivin level in xenograft tumors.

This example provides a proof-of-concept that the dimerization core units in the dimeric interface of "undruggable" homo-dimeric proteins can be used as a target site for drug discovery. Combining computational analysis of the dimeric interface to first identify these core unit with in-silico screening, as demonstrated here, is likely a viable approach that will help succeed in identifying small molecule compounds inhibiting dimerization of the target protein.

The finding that LQZ-7 and its analogues induce survivin degradation is consistent with the concept that exposure of the hydrophobic interface of a dimeric protein often leads to conformational change[24,25], which causes destabilization and degradation of the protein by proteasome or autophagy[26,27]. Interestingly, not all LQZ-7 analogues induced survivin degradation. LQZ-7E had no effect on survivin expression, consistent with its lack of inhibitory effect on cell survival. However, compounds LQZ-7A and 7D are effective in suppressing cancer cell growth but do not appear to induce survivin degradation. This finding is intriguing and suggests that these two compounds may bind to survivin and inhibit its function but do not trigger proteasome-dependent degradation. Alternatively, these compounds may have off-target effects that inhibit cell survival but lost their effect on survivin protein.

It is noteworthy that mutation of the hydrophobic core residue Phe$^{101}$ to Ala$^{101}$ together with mutation of Leu$^{102}$ to Ala$^{102}$ disrupted survivin dimerization, which did not appear to result in survivin degradation[30]. This observation apparently is different from our finding using small molecule inhibitors to disrupt survivin dimerization. Although the cause for this difference is currently unknown, it is possible that monomeric survivin induced by mutation exists as heterodimers by binding to other proteins such as CRM1[30] and does not exist as true monomers in mammalian cells. On the other hand, the monomers induced by a small molecule inhibitor such as LQZ-7F could not form heterodimers with other proteins due to the existence of the compound in the interface. It is also possible that mutation of the dimerization core residues reduced the hydrophobicity of the interface and, thus, the protein could escape from the cell quality control system while binding of the small-molecule compound to the interface may increase the hydrophobicity and attract the quality control system.

It is also noteworthy that a small molecule compound, LLP3, was synthesized previously based on the Abbot8, a survivin inhibitor obtained via a NMR-based screen. LLP3 was thought to bind to the dimerization interface of survivin[31]. However, LLP3 had no effect on survivin dimerization or its expression. Instead, it inhibited interaction between survivin and its partner Ran protein. Thus, it is not clear if LLP3 truly binds to the dimerization interface of survivin. Nevertheless, LLP3 inhibited proliferation of cancer cells but with a much higher $IC_{50}$ of 14-38 µM than that of LQZ-7F.

Methods

MD Simulation Analysis of Water Trafficking.

MD simulations of survivin dimers and water trafficking were carried out using the AMBER9 package as previously described[28]. Crystal structure of survivin dimer with PDB code 1F3H was acquired from RCSB protein databank[2]. Zinc parameters were developed by Y. P. Pang using the cationic dummy atom (cada) approach[41]. Survivin dimer was solvated in a truncated octahedron box with edges no closer than 10 Å to any atom in the solute with appropriate number of counter ions added to neutralize each system. Particle Mesh Ewald (PME) was employed to calculate the long-range electrostatic interactions and the nonbonded cut-off was set to 8.0 Å. Each system was equilibrated by a four-step protocol prior to the 20-ns production MD simulation.

Total buried dimeric interface areas and buried surface areas decomposed to each residue were calculated by areaimol of the CCP4 package. Dimerization core residues that have more than 75% solvent accessible area buried in the dimeric interface were selected. Survivin has one dimerization core unit consisting of four residues: Leu$^{98}$ and Phe$^{101}$ from one chain and same residues from another chain. This dimerization core entity is further validated by its water exchange rate determined via 20-ns water explicit MD simulation as previously described[28,29]. A sphere of 6 Å in radius was drawn from the center of the mass of the core. Water molecules that fell into the sphere during the simulation were monitored and their residue IDs were recorded by VMD program. Then, water molecules from every 20 frames (representing a 200 ps timespan) were pooled and compared with that from the previous 20 frames. Water molecules with residue IDs that existed in the current 20 frames but did not appear in the previous 20 frames were considered water molecules that moved in during the current 200 ps timespan. Water molecules with residue IDs found in the current 20 frames but did not show up again in the next 20 frames were considered water molecules that moved out during this 200 ps timespan.

In-Silico Virtual Screening.

Structure-based in-silico screening was performed as previously described[42,43]. Briefly, The 3-D coordinates of survivin were acquired from PDB code 1F3H. Only one of the two chains was kept and the protein chain was prepared for docking. Molecular surface was calculated using DMS (Distributed Molecular Surface) program. Partial charges and protons were added to the protein by UCSF Chimera Dock Prep module[44]. In-silico dock screening of 200,000 compounds from SPECS's library was performed using UCSF DOCK 6.0 program[45]. The docking of each compound was first scored with the DOCK GRID scoring function[46]. The top-scoring 1000 compounds were analyzed again and re-scored using the AMBER scoring function of DOCK 6.0 package[47]. These compounds were clustered using MOE (Molecular Operating Environment) program and visually examined using the UCSF Chimera ViewDock function. Final 100 compounds were selected based on the combination of GRID and AMBER score, drug likeness (Lipinski's rule of five), and on consideration of maximizing compounds from different clusters.

Non-Denaturing PAGE.

1-μg purified survivin were incubated with 20 μM candidate compounds, DMSO vehicle control, or different concentrations of LQZ-7 before mixing with equal volume of 2× Triton X-100 sample buffer (100 mM Tris, pH 8.0, 20% glycerol, 0.005% bromophenol blue, 2% Triton X-100, and 100 mM DTT) followed by incubation at room temperature for 30 min. After centrifugation at 11,000×g for 10 minutes, the supernatants were separated by electrophoresis on 15% Tris/glycine polyacrylamide gel followed by transfer to PVDF membrane for western blot analysis as previously described[48].

Survival Assays (MTT and Colony Formation).

These assays were performed as previously described[49,50]. Briefly, MTT assay were performed by seeding 2500 cells in 96-well plate and cultured 24 hours before addition of survivin inhibitors at different concentrations and continuous culture for 3 days. The cells were then subjected to MTT assay. For colony formation assay, 100 cells/well were seeded in 6-well plates and cultured for 24 hours before addition of survivin inhibitors or DMSO vehicle. The cells were continuously cultured in the presence of survivin inhibitors or DMSO for 10-14 days followed by staining with crystal violet and counting manually.

Fluorogenic Assay.

Fluorogenic assay was performed as previously described[31]. Briefly, LQZ-7 was pre-incubated without or with 10 μg purified survivin for 30 min at 37° C. followed by determination of fluorescence emission at 485 nm with excitation at 590 nm. A dose response-curve was fitted to an equation describing one-site binding model to determine the $K_d$ of LQZ-7 binding to survivin using GraphPad Prism 4.0 software.

Apoptosis Assay.

Annexin V apoptosis assay was performed as described in the instruction provided by the manufacturer (Invitrogen). Briefly, treated cells were harvested after washing with PBS and then resuspended in annexin-binding buffer (10 mM HEPES, pH17.4, 120 mM NaCl, 2.5 mM $CaCl_2$) at the density of $1\times10^6$ cells/mil. After addition of Alexa Fluor 488 annexin V and propidium iodide, the cells were incubated for 15 minutes at room temperature followed by dilution with annexin-binding buffer and FACS analysis of fluorescence emission at 530 nm and 575 nm with 488 nm excitation.

Half-Life Determination.

The effect of survivin inhibitor on the half-life of survivin was determined as previously described[51]. Briefly, PC-3 or DU145 cells were pre-treated with 2 μM cycloheximide for 1 hour followed by incubation without or with 9 μM LQZ-7 or 5 μM LQZ-7F for different times. The cells were then harvested for Western blot analysis of survivin.

Efficacy Analysis in Xenograft Mouse Model.

For efficacy study, $3\times10^6$ PC-3 cells were injected subcutaneously in the flanks of 10 NOD/SCID mice. When the tumor volume reached about 100 $mm^3$, the mice were randomized into two different groups (5/group) with one group treated by vehicle control and the other by LQZ-7F at 25 mg/kg via IP injection once every three days for total of 8 treatments. Tumor volume and body weight were measured every two days. On the $30^{th}$ day after the initial treatment, mice were euthanized and the tumor tissues were harvested, weighed, and subjected to hematoxylin and eosin (H&E) staining as well as Western blot and immunohistochemistry analysis of survivin.

The examples and embodiments described herein are for illustrative purposes only. Various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES CITED IN THE BACKGROUND AND EXAMPLE SECTIONS

1. Altieri, D. C. Survivin, versatile modulation of cell division and apoptosis in cancer. *Oncogene* 22, 8581-9 (2003).
2. Verdecia, M. A. et al. Structure of the human anti-apoptotic protein survivin reveals a dimeric arrangement. *Nat Struct Biol* 7, 602-8 (2000).
3. Chantalat, L. et al. Crystal structure of human survivin reveals a bow tie-shaped dimer with two unusual alpha-helical extensions. *Mol Cell* 6, 183-9 (2000).
4. Tamm, I. et al. IAP-family protein survivin inhibits caspase activity and apoptosis induced by Fas (CD95), Bax, caspases, and anticancer drugs. *Cancer Res* 58, 5315-20 (1998).
5. Suzuki, A. et al. Survivin initiates procaspase 3/p21 complex formation as a result of interaction with Cdk4 to resist Fas-mediated cell death. *Oncogene* 19, 1346-53 (2000).
6. Kasof, G. M. & Gomes, B. C. Livin, a novel inhibitor of apoptosis protein family member. *J Biol Chem* 276, 3238-46 (2001).

7. Hoffman, W. H., Biade, S., Zilfou, J. T., Chen, J. & Murphy, M. Transcriptional repression of the anti-apoptotic survivin gene by wild type p53. *J Biol Chem* 277, 3247-57 (2002).
8. Mirza, A. et al. Human survivin is negatively regulated by wild-type p53 and participates in p53-dependent apoptotic pathway. *Oncogene* 21, 2613-22 (2002).
9. Zaffaroni, N. et al. Expression of the anti-apoptotic gene survivin correlates with taxol resistance in human ovarian cancer. *Cell Mol Life Sci* 59, 1406-12 (2002).
10. Grossman, D. et al. Transgenic expression of survivin in keratinocytes counteracts UVB-induced apoptosis and cooperates with loss of p53. *J Clin Invest* 108, 991-9 (2001).
11. Fukuda, S. & Pelus, L. M. Survivin, a cancer target with an emerging role in normal adult tissues. *Mol Cancer Ther* 5, 1087-98 (2006).
12. Zhang, M. et al. Adenovirus-mediated inhibition of survivin expression sensitizes human prostate cancer cells to paclitaxel in vitro and in vivo. *Prostate* 64, 293-302 (2005).
13. Zhang, M., Latham, D. E., Delaney, M. A. & Chakravarti, A. Survivin mediates resistance to antiandrogen therapy in prostate cancer. *Oncogene* 24, 2474-82 (2005).
14. Pennati, M. et al. Ribozyme-mediated attenuation of survivin expression sensitizes human melanoma cells to cisplatin-induced apoptosis. *J Clin Invest* 109, 285-6 (2002).
15. Li, F. et al. Pleiotropic cell-division defects and apoptosis induced by interference with survivin function. *Nat Cell Biol* 1, 461-6 (1999).
16. Chen, J. et al. Down-regulation of survivin by antisense oligonucleotides increases apoptosis, inhibits cytokinesis and anchorage-independent growth. *Neoplasia* 2, 235-41 (2000).
17. Olie, R. A. et al. A novel antisense oligonucleotide targeting survivin expression induces apoptosis and sensitizes lung cancer cells to chemotherapy. *Cancer Res* 60, 2805-9 (2000).
18. Williams, N. S. et al. Identification and validation of genes involved in the pathogenesis of colorectal cancer using cDNA microarrays and RNA interference. *Clin Cancer Res* 9, 931-46 (2003).
19. Choi, K. S., Lee, T. H. & Jung, M. H. Ribozyme-mediated cleavage of the human survivin mRNA and inhibition of antiapoptotic function of survivin in MCF-7 cells. *Cancer Gene Ther* 10, 87-95 (2003).
20. Nakahara, T. et al. YM155, a novel small-molecule survivin suppressant, induces regression of established human hormone-refractory prostate tumor xenografts. *Cancer Res* 67, 8014-21 (2007).
21. Rauch, A. et al. Survivin and YM155: How faithful is the liaison? *Biochim Biophys Acta* 1845, 202-220 (2014).
22. Tanioka, M. et al. Phase I study of LY2181308, an antisense oligonucleotide against survivin, in patients with advanced solid tumors. *Cancer Chemother Pharmacol* 68, 505-11 (2011).
23. Wiechno, P. et al. A randomised phase 2 study combining LY2181308 sodium (survivin antisense oligonucleotide) with first-line docetaxel/prednisone in patients with castration-resistant prostate cancer. *Eur Urol* 65, 516-20 (2014).
24. Agashe, V. R., Shastry, M. C. & Udgaonkar, J. B. Initial hydrophobic collapse in the folding of barstar. *Nature* 377, 754-7 (1995).
25. Lins, L. & Brasseur, R. The hydrophobic effect in protein folding. *FASEB J* 9, 535-40 (1995).
26. Kubota, H. Quality control against misfolded proteins in the cytosol: a network for cell survival. *J Biochem* 146, 609-16 (2009).
27. Hochstrasser, M. Intracellular Protein Degradation. in *Cell* (eds. Lewin, B., Cassinmeris, L. & Lingappa, V. R.) Jones & Bartlett Learning, 2007.
28. Liu, J. Y., Li, Z., Li, H. & Zhang, J. T. Critical residue that promotes protein dimerization: a story of partially exposed phe(25) in 14-3-3sigma. *J Chem Inf Model* 51, 2612-25 (2011).
29. Li, Z. et al. *Determinants of* 14-3-3sigma protein dimerization and function in drug and radiation resistance. *J Biol Chem* 288, 31447-57 (2013).
30. Engelsma, D., Rodriguez, J. A., Fish, A., Giaccone, G. & Fornerod, M. Homodimerization antagonizes nuclear export of survivin. *Traffic* 8, 1495-502 (2007).
31. Guvenc, H. et al. Impairment of glioma stem cell survival and growth by a novel inhibitor for Survivin-Ran protein complex. *Clin Cancer Res* 19, 631-42 (2013).
32. Chiou, S. K. & Mandayam, S. NSAIDs enhance proteasomic degradation of survivin, a mechanism of gastric epithelial cell injury and apoptosis. *Biochem Pharmacol* 74, 1485-95 (2007).
33. Chowdhury, S. et al. Histone deacetylase inhibitor belinostat represses survivin expression through reactivation of transforming growth factor beta (TGFbeta) receptor II leading to cancer cell death. *J Biol Chem* 286, 30937-48 (2011).
34. Fortugno, P. et al. Regulation of survivin function by Hsp90. *Proc Natl Acad Sci USA* 100, 13791-6 (2003).
35. Giodini, A. et al. Regulation of microtubule stability and mitotic progression by survivin. *Cancer Res* 62, 2462-7 (2002).
36. Tran, J. et al. A role for survivin in chemoresistance of endothelial cells mediated by VEGF. *Proc Natl Acad Sci USA* 99, 4349-54 (2002).
37. Cheung, C. H. et al. Survivin counteracts the therapeutic effect of microtubule de-stabilizers by stabilizing tubulin polymers. *Mol Cancer* 8, 43 (2009).
38. Rosa, J., Canovas, P., Islam, A., Altieri, D. C. & Doxsey, S. J. Survivin modulates microtubule dynamics and nucleation throughout the cell cycle. *Mol Biol Cell* 17, 1483-93 (2006).
39. Lens, S. M., Vader, G. & Medema, R. H. The case for Survivin as mitotic regulator. *Curr Opin Cell Biol* 18, 616-22 (2006).
40. Kitagawa, M. & Lee, S. H. The chromosomal passenger complex (CPC) as a key orchestrator of orderly mitotic exit and cytokinesis. *Front Cell Dev Biol* 3, 14 (2015).
41. Pang, Y. P. Successful molecular dynamics simulation of two zinc complexes bridged by a hydroxide in phosphotriesterase using the cationic dummy atom method. *Proteins* 45, 183-9 (2001).
42. Neher, T. M., Shuck, S. C., Liu, J. Y., Zhang, J. T. & Turchi, J. J. Identification of novel small molecule inhibitors of the XPA protein using in silico based screening. *ACS Chem Biol* 5, 953-65 (2010).
43. Huang, W. et al. A Small Molecule Compound Targeting STAT3 DNA-Binding Domain Inhibits Cancer Cell Proliferation, Migration, and Invasion. *ACS Chem Biol* 9, 1188-96 (2014).
44. Pettersen, E. F. et al. UCSF Chimera—a visualization system for exploratory research and analysis. *J Comput Chem* 25, 1605-12 (2004).
45. Lang, P. T. et al. DOCK 6: combining techniques to model RNA-small molecule complexes. *RNA* 15, 1219-30 (2009).

46. Meng, E. C., Shoichet, B. K. & Kuntz, I. D. Automated Docking with Grid-Based Energy Evaluation. *Journal of Computational Chemistry* 13, 505-524 (1992).
47. Graves, A. P. et al. Rescoring docking hit lists for model cavity sites: predictions and experimental testing. *J Mol Biol* 377, 914-34 (2008).
48. Zhang, M., Wang, G., Shapiro, A. & Zhang, J. T. Topological folding and proteolysis profile of P-glycoprotein in membranes of multidrug-resistant cells: implications for the drug-transport mechanism. *Biochemistry* 35, 9728-36 (1996).
49. Li, Z. et al. Role of 14-3-3sigma in poor prognosis and in radiation and drug resistance of human pancreatic cancers. *BMC Cancer* 10, 598 (2010).
50. Qi, J., Dong, Z., Liu, J. & Zhang, J. T. EIF3i promotes colon oncogenesis by regulating COX-2 protein synthesis and beta-catenin activation. *Oncogene* 33, 4156-63 (2014).
51. Peng, H. et al. A Novel Two Mode-Acting Inhibitor of ABCG2-Mediated Multidrug Transport and Resistance in Cancer Chemotherapy. *PLoS ONE* 4, e5676 (2009).

We claim:

1. A method of treating cancer comprising administering to a subject in need thereof a therapeutically effective amount of a composition comprising a survivin-targeting compound selected from the group consisting of:

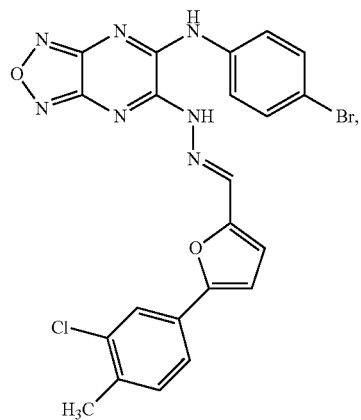

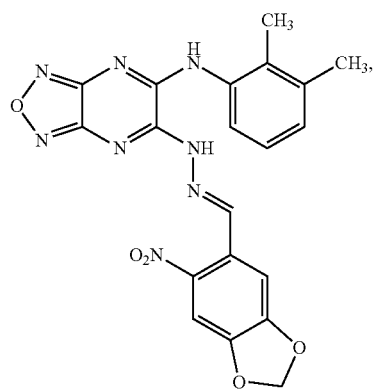

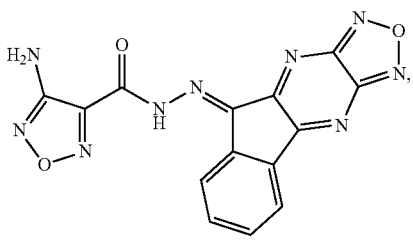 [SMILES: Nc1nonc1C(=O)N/N=C1\c2ccccc2-c2nc3nonc3nc21]

and a pharmaceutically acceptable salt thereof;
whereby the cancer is treated in the subject.

2. The method of claim 1, wherein the survivin-targeting compound is:

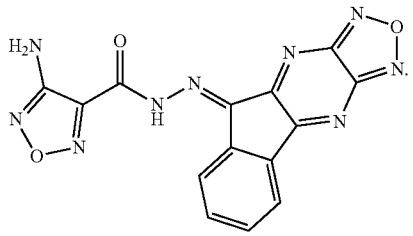 [SMILES: Nc1nonc1C(=O)N/N=C1\c2ccccc2-c2nc3nonc3nc21]

3. The method of claim 1, wherein the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

4. The method of claim 1, wherein the cancer that is treated is selected from the group consisting of breast cancer, colon cancer, lung cancer, pancreatic cancer, prostate cancer, ovarian cancer, and leukemia.

5. The method of claim 4, wherein the cancer that is treated is prostate cancer.

6. A pharmaceutical composition comprising:
(a) a survivin-targeting compound selected from the group consisting of:

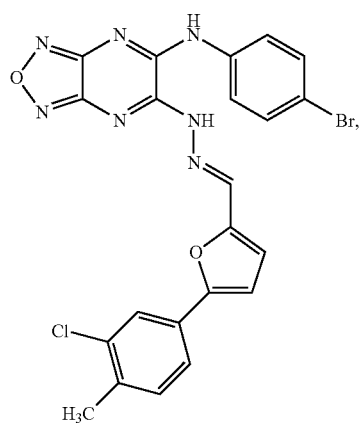

29

-continued

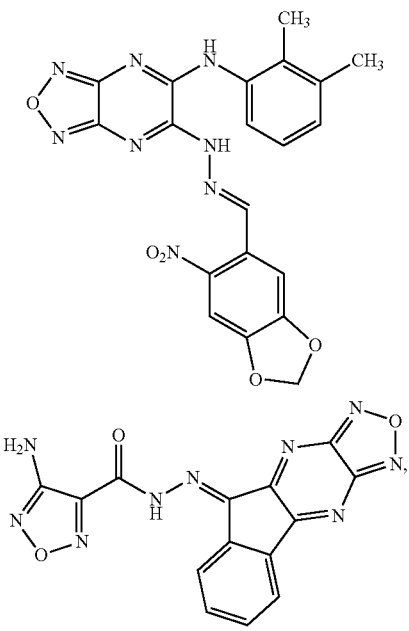

and a pharmaceutically acceptable salt thereof; and (b) a pharmaceutically acceptable carrier.

7. The pharmaceutical composition of claim 6, wherein the survivin-targeting compound is:

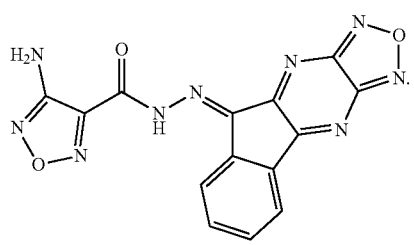 [SMILES: Nc1nonc1C(=O)N/N=C1\c2ccccc2-c2nc3nonc3nc21]

8. A survivin-targeting compound for use in treating cancer in a subject, wherein the survivin-targeting compound is selected from the group consisting of:

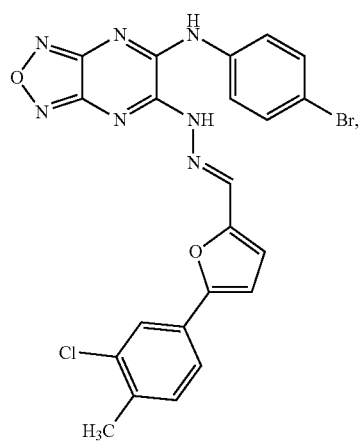

30

-continued

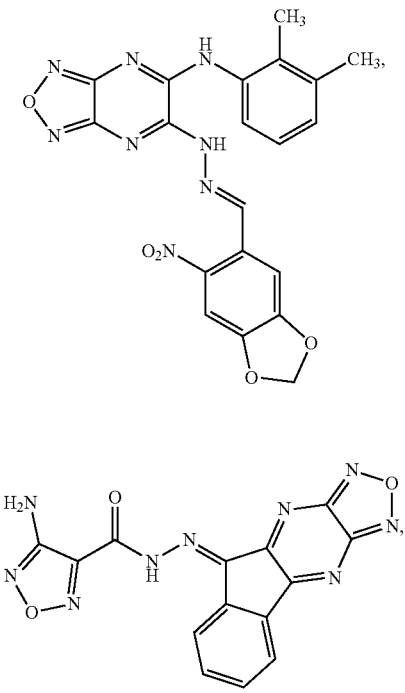

and a pharmaceutically acceptable salt thereof.

9. The survivin-targeting compound of claim 8, wherein the survivin-targeting compound is:

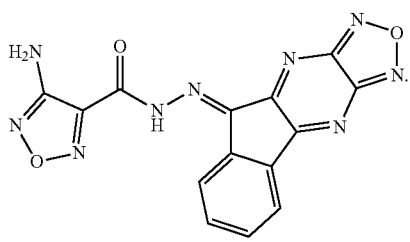 [SMILES: Nc1nonc1C(=O)N/N=C1\c2ccccc2-c2nc3nonc3nc21]

10. The survivin-targeting compound of claim 8, wherein the compound is for use in treating cancer that is selected from the group consisting of breast cancer, colon cancer, lung cancer, pancreatic cancer, prostate cancer, ovarian cancer, and leukemia.

11. The survivin-targeting compound of claim 10, wherein the compound is for use in treating prostate cancer.

12. The survivin-targeting compound of claim 8, wherein the compound is to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

13. A survivin-targeting compound for use in manufacturing a medicament for treating cancer in a subject, wherein the survivin-targeting compound is selected from the group consisting of:

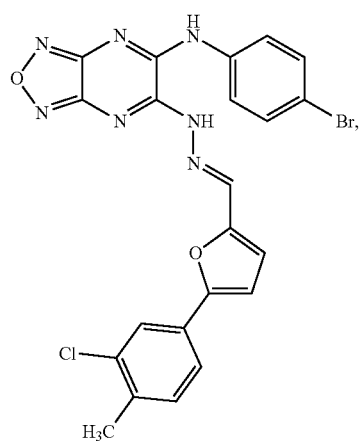

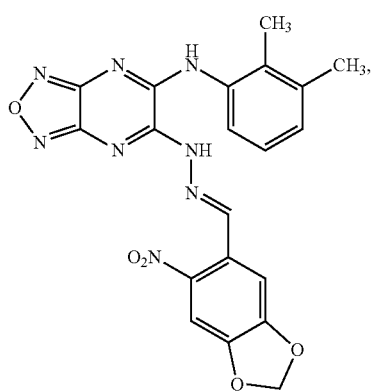

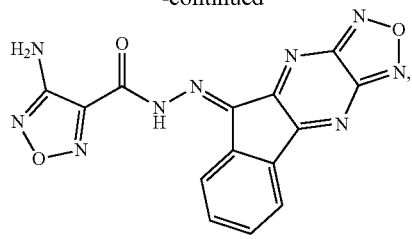

and a pharmaceutically acceptable salt thereof.

14. The survivin-targeting compound of claim 13, wherein the survivin-targeting compound is:

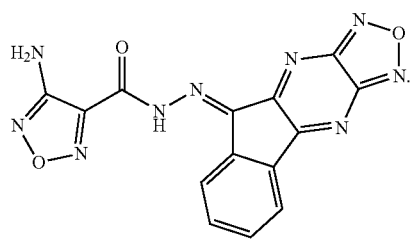 [SMILES: Nc1nonc1C(=O)N/N=C1\c2ccccc2-c2nc3nonc3nc21]

15. The survivin-targeting compound of claim 13, wherein the medicament is for treating breast cancer, colon cancer, lung cancer, pancreatic cancer, prostate cancer, ovarian cancer, or leukemia.

16. The survivin-targeting compound of claim 15, wherein the medicament is for treating prostate cancer.

17. The survivin-targeting compound of claim 13, wherein the medicament is designed to be administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

* * * * *